(12) United States Patent
Gray

(10) Patent No.: US 11,337,061 B2
(45) Date of Patent: May 17, 2022

(54) SYSTEM, METHOD, AND APPARATUS FOR VIRTUALIZING DIGITAL ASSISTANTS

(71) Applicant: Ways Investments, LLC, Lakewood Ranch, FL (US)

(72) Inventor: Mark Edward Gray, Lakewod Ranch, FL (US)

(73) Assignee: Ways Investments, LLC, Sarasota, FL (US)

( * ) Notice: Subject to any disclaimer, the term of this patent is extended or adjusted under 35 U.S.C. 154(b) by 0 days.

(21) Appl. No.: 17/091,465

(22) Filed: Nov. 6, 2020

(65) Prior Publication Data

US 2021/0076206 A1 Mar. 11, 2021

Related U.S. Application Data

(63) Continuation-in-part of application No. 16/857,266, filed on Apr. 24, 2020, now Pat. No. 11,044,364, (Continued)

(51) Int. Cl.
*H04W 12/02* (2009.01)
*H04M 3/42* (2006.01)
(Continued)

(52) U.S. Cl.
CPC .............. *H04W 12/02* (2013.01); *G10L 15/22* (2013.01); *G16H 10/60* (2018.01); *G16H 80/00* (2018.01);
(Continued)

(58) Field of Classification Search
CPC ............. H04M 1/605; H04M 2201/40; H04M 1/72418; H04M 3/42059; H04M 3/42102; H04M 3/4935; H04M 1/575; H04M 1/271; H04M 2250/74; H04M 3/42008; H04M 3/527; G10L 15/22; G10L 2015/223; H04L 63/0272; H04L 61/307; H04L 61/6022; H04L 63/0407; H04W 12/02; G16H 10/60; G16H 80/00; G16H 40/67

See application file for complete search history.

(56) References Cited

U.S. PATENT DOCUMENTS 7,920,843 B2 4/2011 Martin et al.
9,232,040 B2 * 1/2016 Barash .................. H04W 4/90
(Continued)

*Primary Examiner* — Brandon J Miller
(74) *Attorney, Agent, or Firm* — Larson & Larson, P.A.; Frank Liebenow; Justin P. Miller

(57) ABSTRACT

A system and method for providing anonymous communications from a user to a called party includes obtaining a dedicated phone number and creating a user account for the user and assigning the dedicated phone number to the user account. A provider account is created for a digital assistant using the dedicated phone number and the digital assistant is preprogrammed with the user account. The digital assistant is also preprogrammed with a skill for recognizing a specific utterance (e.g. "Call"). Connectivity is provided between the digital assistant and the Internet, for example, using a wireless access point. The digital assistant listens for the specific utterance and, upon recognizing the specific utterance followed by an identification of the called party, the digital assistant initiates a voice call through the Internet to the called party.

19 Claims, 29 Drawing Sheets

Related U.S. Application Data which is a continuation-in-part of application No. 16/656,774, filed on Oct. 18, 2019, now Pat. No. 10,674,014, which is a continuation-in-part of application No. 16/292,458, filed on Mar. 5, 2019, now Pat. No. 1,049,054.

(60) Provisional application No. 62/643,487, filed on Mar. 15, 2018.

(51) Int. Cl.
| | |
|---|---|
| *G16H 10/60* | (2018.01) |
| *G16H 80/00* | (2018.01) |
| *G10L 15/22* | (2006.01) |
| *H04L 9/40* | (2022.01) |
| *H04L 29/06* | (2006.01) |

(52) U.S. Cl.
CPC ... *H04M 3/42059* (2013.01); *H04M 3/42102* (2013.01); *G10L 2015/223* (2013.01); *H04L 63/0272* (2013.01)

(56) References Cited

U.S. PATENT DOCUMENTS

| | | |
|---|---|---|
| 9,300,784 B2 | 3/2016 | Roberts et al. |
| 9,374,698 B2 | 6/2016 | Ahmed et al. |
| 9,390,724 B2 | 7/2016 | List |
| 9,396,645 B2 | 7/2016 | Will et al. |
| 9,543,920 B2 | 1/2017 | Dicks et al. |
| 10,062,387 B2 | 8/2018 | Jiang |
| 10,492,054 B2 * | 11/2019 | Gray ................ H04W 4/90 |
| 10,674,014 B2 * | 6/2020 | Gray ................ G10L 15/22 |
| 11,044,364 B2 * | 6/2021 | Gray ............ H04L 63/0272 |
| 2006/0172720 A1 | 8/2006 | Islam et al. |
| 2007/0158411 A1 | 7/2007 | Krieg |
| 2008/0172232 A1 * | 7/2008 | Gurley ............ G08B 13/1672 |
| | | 704/251 |
| 2008/0305763 A1 | 12/2008 | Wijayanathan et al. |
| 2009/0205041 A1 | 8/2009 | Michalske |
| 2010/0190467 A1 | 7/2010 | Scott et al. |
| 2011/0201302 A1 | 8/2011 | Hatton |
| 2013/0304511 A1 | 11/2013 | Gunter |
| 2014/0046675 A1 | 2/2014 | Hatwood |
| 2014/0150011 A1 * | 5/2014 | Ohno ................ H04N 21/435 |
| | | 725/31 |
| 2014/0370841 A1 | 12/2014 | Roberts |
| 2016/0099908 A1 | 4/2016 | Gelfenbeyn |
| 2016/0373909 A1 | 12/2016 | Rasmussen et al. |
| 2018/0046675 A1 | 2/2018 | Zhou |
| 2018/0068553 A1 | 3/2018 | Amir |
| 2018/0325470 A1 | 11/2018 | Fountaine |
| 2019/0057079 A1 | 2/2019 | Raanani |

* cited by examiner

| USER PVT ID | NAME | HISTORY |
|---|---|---|
| 1112223333 | Smith, J | 3/1/2018 call, no action<br>3/5/2018 call, summoned EMS |
| 1112224444 | Smith, M | 2/5/2018 call, summoned fire – stuck in elev.<br>4/1/2018 operation – left hip replacement<br>5/1/2018 call, fall, summoned fire & EMS |
| 1112225555 | Smith, H | 3/13/2018 call, suicidal, transferred to hot line<br>3/18/2018 call, suicidal, summoned police |

| USER PVT ID | NAME | CONTACTS |
|---|---|---|
| 1112223333 | Smith, J | 555-555-1212 local EMS |
| | | 555-555-1212 local police |
| | | 555-555-1212 staff at XX assisted living |
| | | 555-555-1212 personal - Sister |
| | | 555-555-1212 local fire department |
| 1112224444 | Smith, M | 555-555-1212 personal - Son |
| | | daughter@gmail.com personal - Daughter |
| | | 555-555-1212 local police |
| 1112225555 | Smith, H | 555-555-1212 Priest |
| | | 555-555-1212 Counseler |
| | | 555-555-1212 Preferred Suicide hotline |
| | | 555-555-1212 local police |

SYSTEM, METHOD, AND APPARATUS FOR VIRTUALIZING DIGITAL ASSISTANTS

CROSS-REFERENCE TO RELATED APPLICATION

This application is a continuation-in-part of U.S. patent application Ser. No. 16/857,266 filed on Apr. 24, 2020, which is a continuation-in-part of U.S. patent application Ser. No. 16/656,774 filed on Oct. 18, 2019 now U.S. Pat. No. 10,674,014 issued Jun. 2, 2020, which is a continuation-in-part of U.S. patent application Ser. No. 16/292,458 filed on Mar. 5, 2019 now U.S. Pat. No. 10,492,054 issued Nov. 26, 2019, which claims the benefit of U.S. provisional application No. 62/643,487 filed on Mar. 15, 2018, the disclosure of which are incorporated by reference.

FIELD

This invention relates to the field of providing help to a user and more particularly to a system for private communications with a second party such as a health care provider.

BACKGROUND

In recent years, many companies have introduced devices that accept voice commands and take actions based upon those voice commands. Some such devices operate on smart phones, but lately, many companies are producing what is known a digital assistant or "smart speakers" which are typically stand-alone devices that are connected to a network (e.g. the Internet). These digital assistants listen for voice commands, recognize and analyze the voice commands and act on those voice commands through a network. Often, such devices utilize a keyword to initiate action. For example, one device from Amazon® is Alexa®. In order to issue a command to this device, the user must first say the keyword, "Alexa", or other optional Wake words, followed by the command. For example, "Alexa, what is the weather in Aruba today?" This keyword is important so the digital assistant does not overhear and interpret normal conversations and act on what is heard. For example, if you were on the phone and said to the other party, "did you turn off the lights," without this keyword, the digital assistant might just turn off the lights in your house.

There are many uses for these digital assistants such as, reading/answering email or texts, operating connected appliances within the home, controlling the playing of music, looking up information/trivia, etc.

Unrelated to these digital assistants are medical emergencies, predicaments, or medical alerts. Many people of all ages, though concentrated on those in their golden years, run into situations in which they need help, for example, after a fall, getting stuck in a home elevator, or the onslaught of a serious medical condition such as a stroke or heart attack. If another person is in the same home or nearby, the person having the medical emergency or other hazard can shout to get that person's attention, but what about those who are alone, perhaps because others that live with them are out of the home, or they live alone. Shouting will not solicit help.

A medical alarm is an alarm system designed to signal the presence of such an event that requires urgent attention and, if needed, to summon emergency medical personnel. Other terms for a medical alarm are Personal Emergency Response System ("PERS") or medical alert. Elderly people and disabled people who live alone commonly use/require medical alarms.

Typical medical alarm systems in use today have a wireless pendant or transmitter that is activated after an event has occurred. When the transmitter is activated, a signal is transmitted and relayed to an alarm monitoring company's central station. The central station is staffed with trained personnel to assess the situation and contact other emergency agency or other programmed phone numbers. In some cases, personnel are dispatched to the site where the alarm was activated.

Such medical alarm systems work well when properly installed, when the batteries have sufficient charge and when the user remembers or agrees to wear them. However, since traditional medical alarm systems are, at least in part, user operated, there are problematic drawbacks. For example, if a user gets up in the middle of the night to go to the bathroom without their device, and falls or becomes ill and cannot reach their emergency device, or telephone; then they cannot get the emergency help they need, rendering the medical alert useless. Often, users have complications during the night, when trying to reach the bathroom. Often such users are not in possession of their medical alert device.

Furthermore, such medical alarm systems rely on user operations that requires users to change their behavior, making current medical alarm systems inherently susceptible to users' personal limitations, proclivities, and flaws—putting reliance on the user to remember to recharge the battery and consistently wear a pendant, wrist band, panic button, or other device for the entire day and night. Some users, however, do not want to wear the alarm pendant or wrist band because of aesthetics and/or inconvenience and/or privacy, rendering the device useless when needed. Also, some users forget to don or wear the device and the device may not be within reach when they need it most. Additionally, some users forget to charge the device regularly and the device simply shuts down and ceases to operate until recharged. In fact, approximately 30% of all users of such devices cancel medical alert service annually, possibly due to the fact that they no longer wear or use the device, despite the fact that the user is still in need of a medical monitoring. In an independent research study, 83% of subscribers to medical alert services did not have their medical alert wearable device within reach in a slip and fall at home and resulted in five (5) minutes or longer stranded on the floor and unable to get up without assistance.

Additionally, as of this writing, both Amazon® Alexa® and Google Assistant® and other digital personal assistants (DPA) are not permitted to dial 911 by operating system programming. If a voice command is given to "Call for Police," "Call for a Doctor," "Call for an Ambulance," fire or other emergency is given, those commands are blocked by the digital personal assistant, by design. One of the issues with issuing calls directly to 911 is that greater than 90% of all issued alarms from electronic alarm systems in the United States are deemed false alarms. This is a significant problem in the industry, and thus, any types of digital personal assistants are currently disabled form making unverified calls to 911.

Privacy is also of the utmost importance. In the United States, there is a set of laws commonly called HIPAA, which stands for the Health Insurance Portability and Accountability Act. HIPAA provides for stiff penalties for offenses in which medical personnel divulge any private medical information regarding a patient. Therefore, anyone involved with providing any part of a medical alarm system must be thoroughly trained and monitored to treat any information confidentially, as release of any health-related information is a possible violation of the law related to HIPAA.

These digital assistants are perfect for summoning help, especially as described in the parent applications utilizing a server and call center for connecting an agent to determine the reason for help and dispatching the proper type of help, if any is needed, depending upon the nature of the call for help. Further, having these digital assistants within the users' living quarters opens other features of the digital assistants for the users. For example, it is fully anticipated that the users be able to listen to music, ask questions like "keyword—what is the weather," etc. It is also anticipated that the digital assistants be used in other medical-related transactions such as tele-medicine and communicating with medical professionals. For example, the user might say "keyword—connect me with doctor Smith." In using a digital assistant in such a way, some of the information that transpires between the digital assistant and the other end is available, for example, to workers and agents of the company providing the digital assistant service. Therefore, providers are reluctant to sell or advertise digital assistants for such uses as this service would not be HIPPA compliant.

What is needed is a system that provides voice communication and connectivity between a digital assistant and a called party (e.g. health care provider) providing privacy for Protected Medical Information ("PHI") by omitting identification information that might correlate to the user of the digital assistant.

SUMMARY

The present invention relates to digital assistants and communications with medical organizations, either by voice or by data. More particularly, the digital assistants are used to connect to a medical service or provider to interact and share medical data that, in some embodiments, includes Protected Medical Information ("PHI").

In one embodiment, a system for anonymous communications from a user to a called party is disclosed. The system includes a digital assistant that is preprogrammed with account information and a skill for recognizing a preprogrammed specific utterance. The digital assistant is also configured with a dedicated phone number that is not assigned to the user. An access point (e.g. a wireless access point) is provided and the digital assistant is configured to wirelessly communicate with the wireless access point as the wireless access point is connected to the Internet such that, the digital assistant is enabled to communicate with the Internet through the wireless access point. When the digital assistant recognizing the specific utterance followed by an indication of the called party, the digital assistant initiates a voice connection to the called party and when the called party receives caller-id data regarding the voice connection, the caller-id data comprises the dedicated phone number. After accepting the voice connection, the user is in audio communication with the called party.

In another embodiment, a method for providing anonymous communications from a user to a called party includes obtaining a dedicated phone number and creating a user account for the user and assigning the dedicated phone number to the user account. A provider account is created for a digital assistant using the dedicated phone number and the digital assistant is preprogrammed with the user account. The digital assistant is also preprogrammed with a skill for recognizing a specific utterance (e.g. "Call"). Connectivity is provided between the digital assistant and the Internet, for example, using a wireless access point. The digital assistant listens for the specific utterance and, upon recognizing the specific utterance followed by an identification of the called party, the digital assistant initiates a voice call through the Internet to the called party.

In another embodiment, a system for providing anonymous communications from a user to a called party includes a dedicated phone number that is obtained for the user. A provider account is created for a digital assistant using the dedicated phone number to protect the privacy of the user. An account for the user is created in the system for providing help, the account having information regarding the user and the account having the dedicated phone number. The digital assistant is preprogrammed with a skill recognizing a specific utterance and the digital assistant is pre-configured to connect to the Internet (e.g. through a wireless network adapter). After the specific utterance followed by an identification of the called party is detected by the digital assistant, the digital assistant initiates a voice call to the called party. Without knowledge of the dedicated phone number, any voice data intercepted from the voice call by an eavesdropper is anonymous and does not correlate to the user.

To protect such Protected Medical Information ("PHI"), each digital assistant is virtualized in such a way that any individual or system gaining access to any of the data/voice sent or received by the digital assistant isn't associated with the user of the digital assistant. In other words, from the perspective of the individual or system that has gained access to this data, it is simply random data related to somebody, but the individual or system has no way to correlate the date/voice to any one person. For example, if an eavesdropper hears "your diagnosis is cancer," the eavesdropper only knows that somebody has just been given a diagnosis of cancer, but there is no way for the eavesdropper to know who has this diagnosis and, therefore, without being able to associate the captured data with an individual, privacy is maintained.

Such privacy is not available from existing digital assistants that are configured using information about the user such as home address, email address and phone numbers. Further, these digital assistants connect to an existing home network (e.g. Wi-Fi) that has a digital modem with an address (MAC address) that identifies the home in which it is located, all of these identifying items prevent an existing digital assistant from being used to convey information on which one can rely upon privacy. A person can certainly use such digital assistants to convey private information, but there are no provisions to assure that such private information is safe. As in the above example, the eavesdropper is not only able to see the data ("you have cancer"), but is also able to associate the data with a location and possibly a single person, especially if that person lives alone.

The system for virtualizing digital assistants provides protection of Protected Medical Information ("PHI"). Instead of making sure that nobody except the intended recipient can view/access such Protected Medical Information, the system for virtualizing digital assistants removes or virtualizes addressing information that previously allowed others to correlate protected medical information with the person for which that information applies. By virtualizing the sender/recipient of the protected medical information, any unintended recipient will not be able to correlate the protected medical information to a person. As an example, someone intercepting a message from a doctor to a patient telling the patient information regarding a prescription might know the sender (e.g. Doctor Smith), but will only have addressing information for the patient that is virtual and unlisted. This is akin to knowing that someone in the world is being prescribed a certain medication, but there is now way to know who is being prescribed the medication and, therefore, even though anyone is able to see the protected medical information, without being able to correlate such information to a particular person, such information is useless to an unwanted interceptor. Of course, the parties sharing the protected medical information need to make sure that identifying information does not appear in the data that is shared.

In relationship to digital assistants and the present application, by virtualizing address information of the digital assistants (related phone number and IP address), the digital assistants can be used to contact health care providers and can be used to search the web for sensitive data, particularly related to health, without divulging who is contacting the health care providers or who is searching. For example, a person who just found out they have a contagious disease, may not want others to know that they are searching the web for information and cures for that disease. Likewise, if that person calls a health care provider that specializes in that disease, that person may not want others to know that they are working with such health care providers, etc. By registering the virtualized credentials of the person's digital assistant(s) with health care provider, that person will be known to the health care provider but no one else. Therefore, after such registration, when this person contacts the health care provider using the digital assistant(s), the health care provider will know who is calling without needing to ask for a name and, therefore, unless identification is voluntarily disclosed, an eavesdropper will have no way to correlate any information transpired between the digital assistant(s) and the health care provider, typically voice conversations.

In other embodiments, the digital assistants are powered by a continuously recharged battery-backup base unit which gives the user several hours of battery back-up in the instance of a power outage. The battery-backup base units are powered by household power, e.g. from a wall outlet continuously eliminating the need for the user to remember to recharge them.

In other words, the system for providing help monitors and waits for a user's call for help from anywhere in their home within listening distance of one or more digital assistants. The user is not required to change their normal behavior by wearing an electronic device or worry about battery charge levels in such electronic device.

Additionally, the system for providing help is 911-non-compliant, as an agent (e.g. trained emergency professional) within the process assesses what is needed so as to facilitate the 911 call after the extent of the situation is known.

In other embodiments, a system for providing help is disclosed including a preprogrammed kit for deployment to a premise. The preprogrammed kit includes a digital assistant that is preprogrammed with account information and at least one skill for recognizing a preprogrammed specific utterance. The kit also includes a virtual private network repeater that has a wired connection for connecting to an existing modem and a wireless transceiver, whereas communications between the wireless transceiver and the digital assistant are preprogrammed including addresses and passwords. The system further includes a plurality of agent computers, each connected to a server by a data network. The digital assistant is preprogrammed to transmit a request for help through the virtual private network repeater to the server upon the digital assistant recognizing the specific utterance and after receiving the request for the help, the server assigns one of the agent computers and forwards the request for the help to the one of the agent computers.

In other embodiment, a method of providing help is disclosed including generating a unique user email address, creating a user account and assigning the unique user email address to the user account, and creating a provider account with a provider using the unique user email. A preprogrammed kit is provided (to a user) comprising a virtual private network repeater and at least one digital assistant. Each digital assistant preprogrammed with an address of the virtual private network repeater, a password for accessing the virtual private network repeater, and the user account, preprogramming a skill into each of the digital assistant(s) for recognizing a specific utterance. Connectivity is provided between each of the digital assistant(s) and a server through the virtual private network repeater. Each of the digital assistant(s) listen for the specific utterance and, upon recognizing the specific utterance by any of the digital assistant(s), that digital assistant sends a request for help to the server through the virtual private network repeater. Upon receiving the request for the help, the server forwards the request for help to an agent computer.

In other embodiment, a system for providing help is disclosed including a unique user phone number generated for a user of the system for providing help for protecting privacy of the user, a provider account created using the unique user phone number to protect the privacy of the user, and an account for the user created in the system for providing help, the account having information regarding the user and the account having the unique user phone number. A preprogrammed kit is provided comprising a virtual private network repeater for connecting to an existing modem and a digital assistant. The digital assistant is preprogrammed with a skill recognizing a specific utterance and the digital assistant is pre-configured to connect with the virtual private network repeater. After the preprogrammed specific utterance is detected by the digital assistant, the digital assistant initiates a request for help and a call is made to the server having a caller-id of the unique user phone number, the server answers the call, recognizes the unique user phone number, assigns an agent computer, and forwards the request for help to the agent computer.

Further embodiments include using digital assistants in Adult Living Facilities. In recent years, Adult Living Facilities have been developed with three primary levels of care: Independent Living, Assisted Living and Skilled Nursing Facilities. In some instances, there have been additional designations for Memory Care facilities. As of this writing Roughly one million Americans reside in senior care facilities. This number is expected to almost double by 2030.

The assisted living industry is made up of a variety of senior care services, including assisted living facilities. The Census divides the assisted living facilities industry into two major categories: continuing care retirement communities (NAICS 623311) and homes for the elderly (NAICS 623312). The primary distinction between the two is the presence of nursing care: continuing care retirement communities provide on-site nursing facilities, while homes for the elderly do not or are not required to have on-site nurses.

Assisted living facilities provide excellent services for seniors who wish to remain independent but still need some assistance with daily living. Types of assistance offered in assisted living facilities include help with bathing, dressing, eating, grooming and getting around. There are a variety of options available in the assisted living facilities industry, making them popular with seniors.

Future industry growth will be spurred by the 77 million Baby Boomers planning to retire over the next two decades. With life expectancy continuing to increase in the U.S., many individuals who retire at 65 will have to decide where to spend the remaining twenty or more years. This is expected to increase demand for assisted living services, therefore the need for Adult Living Facilities and supporting technologies to provide support for residents and staff is well established and provides for the increased social good.

In such Adult Living Facilities, a digital assistant is placed in each resident's room, or if occupied by multiple residents in the same shared-room environment with the option of providing a digital assistant next to each resident with a different preprogrammed specific utterance for each user-resident.

Also, at the Adult Living Facility's location, a digital assistant is positioned at each staff station (e.g. nurses' station), and at one or more desks of administrative staff. One or more digital assistants are positioned strategically around common areas, living areas or shared recreation areas. Having digital assistants deployed across the Adult Living Facilities facility also provides most or all of the occupied space with an effective paging system. In such, broadcast announcements are provided for a nurse or staff member to make facility-wide, non-emergency announcements such as, meal-time reminders, invitation to join activities in the recreation area, or any other event. This is especially useful in Memory Care facilities. In some embodiments, automatic, non-emergency announcements are distributed to all or selected digital assistants such as, meal-time reminders, reminders of activities in the recreation area, or any other similar calendar items. This is especially useful in alleviating staff workload in the automation of redundant tasks.

In an emergency, residents speak the preprogrammed specific utterance (e.g. "Alexa, Call for Help") which will quickly connect them by two-way voice to the staff/nurse's station which is preferably staffed 24/7. If the call for help is unanswered by the staff/nurse, the digital assistant that is reporting the emergency is connected by two-way voice to an urgent response center which is staffed with agents 24 hours of each and every day. This provides for overflow of emergency calls when the Staff/nurse is otherwise occupied or momentarily away from the Staff/nurses station.

Having digital assistants in many rooms, in some embodiments, intercom communication is available by the residents and/or the staff/nurses. In the past, residents pressed a call-button to page a nurse, requiring the nurse to walk to answer each resident's request, which may or may not be urgent. Connecting all residents to other residents and to staff/nursing by two-way voice increases efficiency and often shortens response times to residents' requests.

For memory care residents, often the same questions is asked repeatedly because the patient does not recall just having asked the same question moments ago, such as "what time is it?" Digital assistants will answer these questions without becoming frustrated or annoyed with the resident. In some cases, these types of memory care resident questions are stressful to staff and have been cited as one of the causes for high turnover of Adult Living Facility's or Memory Care staff. The digital assistant's interaction with residents will reduce isolation, depression and loneliness which has been cited by the Journal of the American Medical Association as a negative health impact equivalent to smoking 15 cigarettes per day, often resulting in a reduction of the individual's life expectancy by as much as 8 years.

It has been reported by adult living facilities and memory care operators that residents go missing from their rooms for prolonged periods requiring an impromptu search for the resident, utilizing several staff members time. The system of facility-wide digital assistant deployment provides for paging of a resident and allowing two-way communication with the staff/nurses' station which reduces the need for a further search for the resident.

By deploying digital assistants in each patients' room, in some embodiments, each patient will have the ability to make and receive phone calls just by voice command as well as the ability to send and receive voice or text (SMS) messages. In some embodiments, the digital assistants provide smart voice assistance for control of lights, thermostats, television and other devices. Such features will increase safety for residents who have mobility issues and reduce isolation for residents while decreasing work-load on nurses and staff to do basic task such as turning lights on and off.

The disclosed system and method anonymizes each resident and protects sensitive health information as required under HIPAA compliance, a necessary feature for the deployment of digital assistants in assisted living facilities or memory care facilities. Absent of such security protocols, the assisted living facilities or memory care facilities owner/operators would be at risk for significant HIPAA violations and fines making the use of digital assistants, and their many stated benefits, a high risk.

As lifeline functionality is needed during a power outage, the disclosed system deploys internet (e.g. Wi-Fi) access points to provide sufficient coverage of the facility, with added universal power supplies powering each access point and digital assistants in each room, staff/nurse stations, administrative desks, and digital assistants located in common areas. In some embodiments, each resident's digital assistant will be anonymized and assigned on the network by room number, or in the case of shared rooms as room 101-A, 101-B, etc. Through use of an encrypted secure database, only staff members or urgent response operators at an offsite call center have access to the secure data including the name of the resident and other private health information, per HIPAA compliance standards.

BRIEF DESCRIPTION OF THE DRAWINGS

The invention can be best understood by those having ordinary skill in the art by reference to the following detailed description when considered in conjunction with the accompanying drawings in which:

FIGS. 7-10 illustrate exemplary user database data.

DETAILED DESCRIPTION

Figure 1:
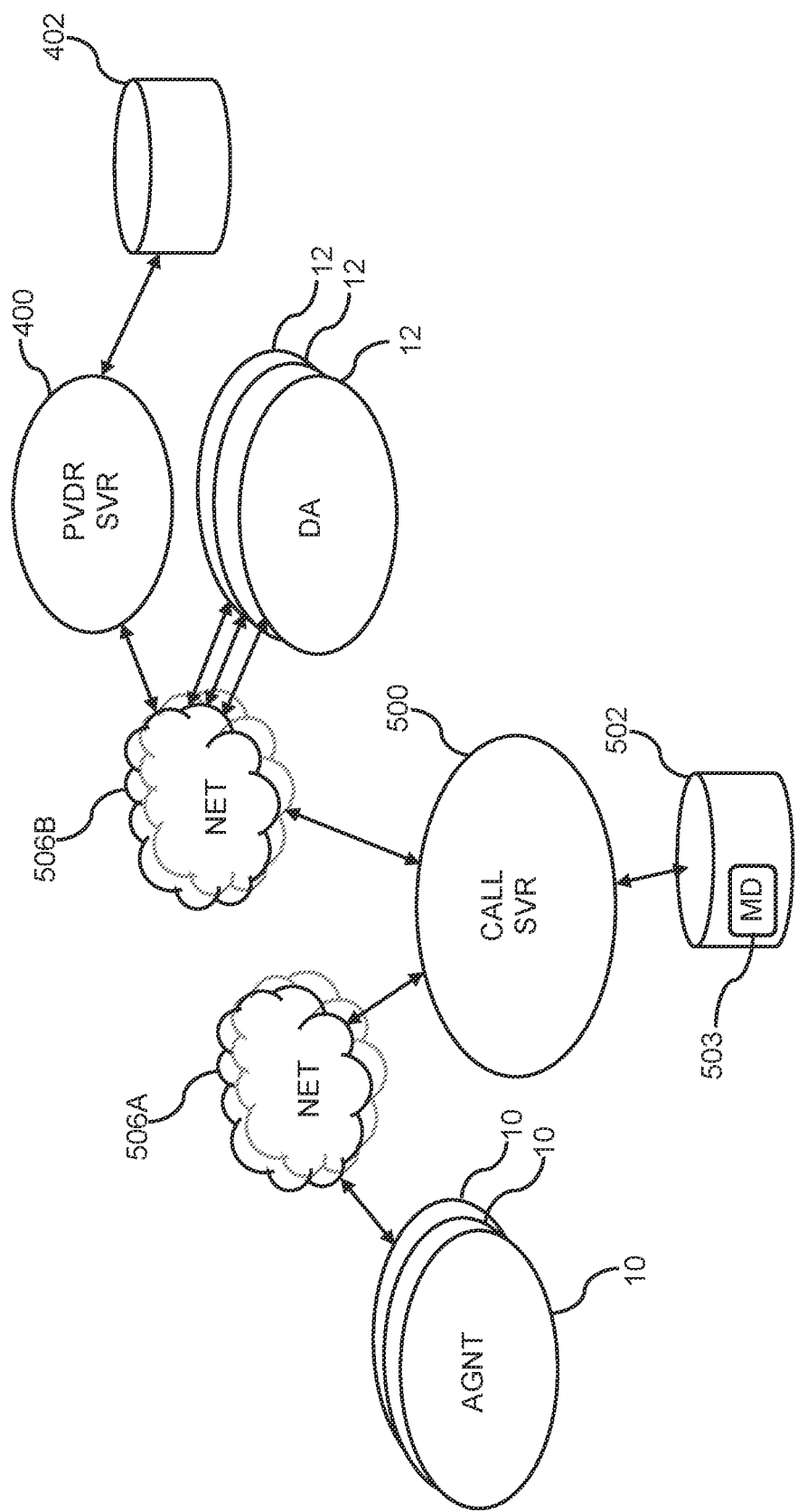
FIGS. 1 and 1A illustrate data connection diagrams of system for providing help.

Reference will now be made in detail to the presently preferred embodiments of the invention, examples of which are illustrated in the accompanying drawings. Throughout the following detailed description, the same reference numerals refer to the same elements in all figures.

Throughout this description, the term, "computer," refers to any system that has a processor and runs software. One example of such is a personal computer. The term, "digital assistant," refers to any device that interprets voice commands and takes action or responds to those commands, for example, but not limited to, the Alexa® device from Amazon®, the Google® Home device, smartphones, etc. The term, "user," refers to a human that interfaces with the digital assistant through voice commands. The term, "agent," refers to a person who receives notice of an issue with the user and determines the appropriate next step, for example, sending help or calling emergency services (e.g. 911 or direct dispatch of emergency services from the appropriate nearby first responder agency on behalf of the user.

Figure 1A:
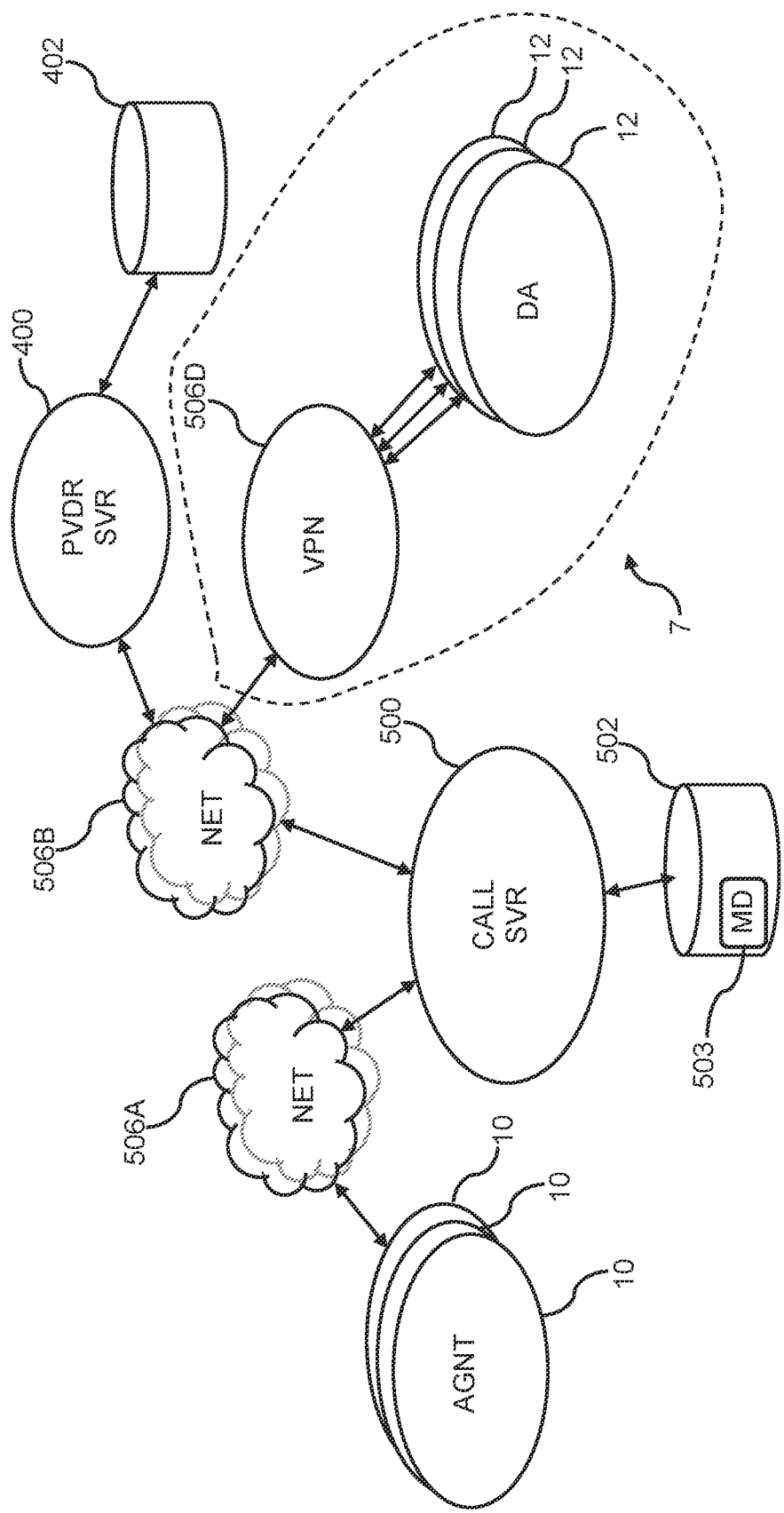

Referring to FIGS. 1 and 1A, data connection diagrams of the exemplary system for providing help are shown. In this example, agent computers 10 (e.g., personal computers) communicates through a first network 506A (e.g. the Internet, local area network, etc.) to a call center server computer 500. The agent computers 10 are staffed with agents; people who are trained and have tools for dealing with medical or non-medical emergencies such as a user falling, having a severe medical condition (e.g. stroke or heart attack), or being stuck in an elevator.

The call center server computer 500 (e.g. a computer, a server or an array of servers or computers) provides access security, allowing only those agents that are authorized to access the call center server computer 500, and therefore, to process incoming calls.

Although one path between the agent computers 10 and the call center server computer 500 is through the first network 506A as shown, though any known data path is anticipated. For example, a local area network, Wi-Fi combined with a wide area network, which includes the Internet.

The call center server computer 500 transacts with the agent computers 10 through the first network(s) 506A, presenting information regarding incoming requests for help, as permitted by privacy rules. In some embodiments, a two-way voice communication is set up between the agent computer 10 and the digital assistant 12 that initiated the request for help. In some embodiments, the agent computers 10 and/or the call center server computer 500 are equipped with tools to facilitate obtaining the proper help in response to the request for help including dispatch of private staff to the residence and escalation contacts up to and including a connection to emergency services (e.g. 911).

The call center server computer 500 (and/or the agent computers 10) has access to data storage 502. In some embodiments, the data storage includes a database, or managed account database, that contains data for each user and, preferably, anonymizes the user's identity to the digital assistant providers as well as to potential hackers of the digital assistants 12. The database contains data used in routing from the digital assistants 12 to the agent computers 10, historical data such as information regarding prior requests from the same location (digital assistants 12), call logging such as dates, times, durations, content, etc., and security to the users of the digital assistants 12 and access controls. In some embodiments, the database includes medical data 503 regarding each user. The agent at the agent computer 10 is trained to respond to medial and non-medical emergencies. Armed with this medical data 503, when the agent at the agent computer 10 receives an indication of help needed by a user, the medical data 503 is accessed to provide the agent with knowledge of the user's pre-existing conditions to help the agent determine the nature and extent of the issue and to dispatch appropriate help to the user based upon information gleaned from the user and information from the medical data 503. For example, if the user is experiencing symptoms that indicate that the user is having a heart attack and the information from the medical data 503 indicates that the patient is bariatric, the medical help that is dispatched by the agent is informed of such as heavy lifting may be required once the user is stabilized.

Any number of digital assistants 12 is anticipated. The digital assistants 12 monitor sound and analyze the sound for specific utterances. Of interest to the system for providing help is specific utterances that are configured to request help such as "Alexa, Call for help" or similar. In the embodiment shown, the digital assistants communicate through the second network 506B (e.g., the Internet as well as internal/external networks) to the call center server computer 500, typically when and after the specific utterances 5 (see FIGS. 6 and 6A) that request help are detected. The second network 506B is any single or combination of network technologies, including, but not limited to local area networks (e.g. Ethernet), wireless networks (e.g. Wi-Fi or 802.11x), cellular data networks (e.g. GSM, CDMA, TDMA, LTE), of any type and configuration of network(s).

As many homes already have a second network 506B that often has considerable bandwidth, often having a modem 15 (see FIG. 11A) such as a cable modem or fiber access modem, and a wireless router (e.g. a Wi-Fi router); in some embodiments, the digital assistants 12 connect directly to the existing second network 506B. This requires that each digital assistant be configured to connect to the existing second network 506B which requires administration by way of another device that is connected to the second network 506B and providing credentials so that each digital assistant 12 is able to connect to the second network 506B. Often, homeowners have forgotten their credentials (e.g. password) and/or are not wanting to provide their passwords to other people/organizations, making installation difficult. Further, as the technical capabilities of many individuals that might need the help and features of the disclosed system for providing help are often minimal, installing one or more digital assistants 12 in a home will require an installer to visit the home, for example, a professional installer or a family member of the individual in need. As evident in today's environment and current virus situation, many individuals do not want a strange person in their home.

To totally alleviate the need for an installer, the configuration of FIG. 1A includes a virtual private network repeater 506D that is preconfigured to communicate with one or more of the digital assistants 12 that are provided at the time of purchase or additional digital assistants that are later programmed with security codes to access the virtual private network repeater 506D. The virtual private network repeater 506D plugs directly into the modem 15 (e.g. cable modem, fiber modem) of the second network 506B, for example, using a provided Ethernet cable. In this way, the individual in need simply unpacks the virtual private network repeater 506D and digital assistants 12, connects power to such, and plugs in the provided cable, connecting the virtual private network repeater 506D and the existing modem 15, without the need to administer any devices in the home as everything is pre-configured. Not only are the digital assistants 12 pre-programmed to communicate directly to the virtual private network repeater 506D over wireless connections using pre-programmed credentials of which there is no need for the individual in need to know or understand, each digital assistant 12 is protected by the virtual private network repeater 506D by enhanced encryption and firewall protection. Therefore, even it the modem 15 and any existing wireless routers are poorly installed (e.g. with weak encryption, simple passwords, lack of firewall protection), the digital assistants 12 are virtualized by the virtual private network repeater 506D, protecting confidential medical information that may be shared between the agents at the agent computer 10 and the individual serviced by the digital assistants 12. This being said, the individuals serviced by the digital assistants 12 are still free to use any other feature of the digital assistants 12 (e.g. asking the time or weather or playing music).

It is known in the industry that a virtual private network (VPN) creates a connection between devices. In this disclosure, the virtual private network repeater 506D is a self-contained device that provides secure connections between one or more digital assistants 12 and the call center server computer 500. In this way, the IP address and the actual location of all digital assistants 12 are hidden and instead, the IP addresses of the virtual private network repeater 506D and a virtual location is presented to the Internet. Websites that are visited by the digital assistants 12 do not have visibility and/or access to the IP address of the digital assistants 12. In this way, a hacker looking to steal the user's information is stopped. Data passing through the virtual private network repeater 506D is encrypted and hidden so hackers cannot gain access to sensitive information such as medical information.

The modem 15 and internet service provider will only see encrypted information. Further, the virtual private network repeater 506D prevent marketers from tracking activity by the digital assistants 12. Marketers who would track user's activity to target their advertisements will no longer be able to track because a new IP address is issued for each connection.

In some embodiments, a preprogrammed kit 7 is provided to the user/premise/home. This preprogrammed kit 7 includes the virtual private network repeater 506D with cable for connecting to an existing modem 15 and one or more digital assistants 12 that are preprogrammed with the needed skills and with preprogrammed connections (addresses and passwords) for connection to the virtual private network repeater 506D. In this way, the user 4 receives the preprogrammed kit 7, the user need only connect the virtual private network repeater 506D an existing modem 15 (potentially using the cable provided in the preprogrammed kit 7) and plug in each of the one or more digital assistants 12. Being that the virtual private network repeater 506D is physically connected to the modem 15, there is no need to program a password and, because the digital assistant(s) 12 are already programmed with credentials and addresses for accessing the virtual private network repeater 506D as well as account information and skills, once powered, the digital assistant(s) 12 will correctly connect to the call center server computer 500 when the specific utterance is spoken.

In some embodiments, the digital assistant(s) 12 respond to the specific utterances 5 (e.g. "Alexa, Call for help") by interfacing with a service provider's server 400, a server owned and maintained by the provider of the digital assistant 12 to initiate the call. The service provider's server 400 has provider accounts stored in a provider's database 402. The service provider's server 400 receives the request for the call from the digital assistant 12 and initiates a phone call, e.g. by Voice over IP through the network 506B to the call center server computer 500. The call center server computer 500 receives the call from the service provider's server 400 and uses a caller-id of the call access user records (e.g. from data storage 502) to determine the name, phone number, and location of the user 4; history of this user's 4 issues; medical information regarding the user 4 (e.g. heart conditions, medications, mobility); local support staff locations and contact information (e.g. roaming staff, staff in assisted living); etc.

Figure 2:
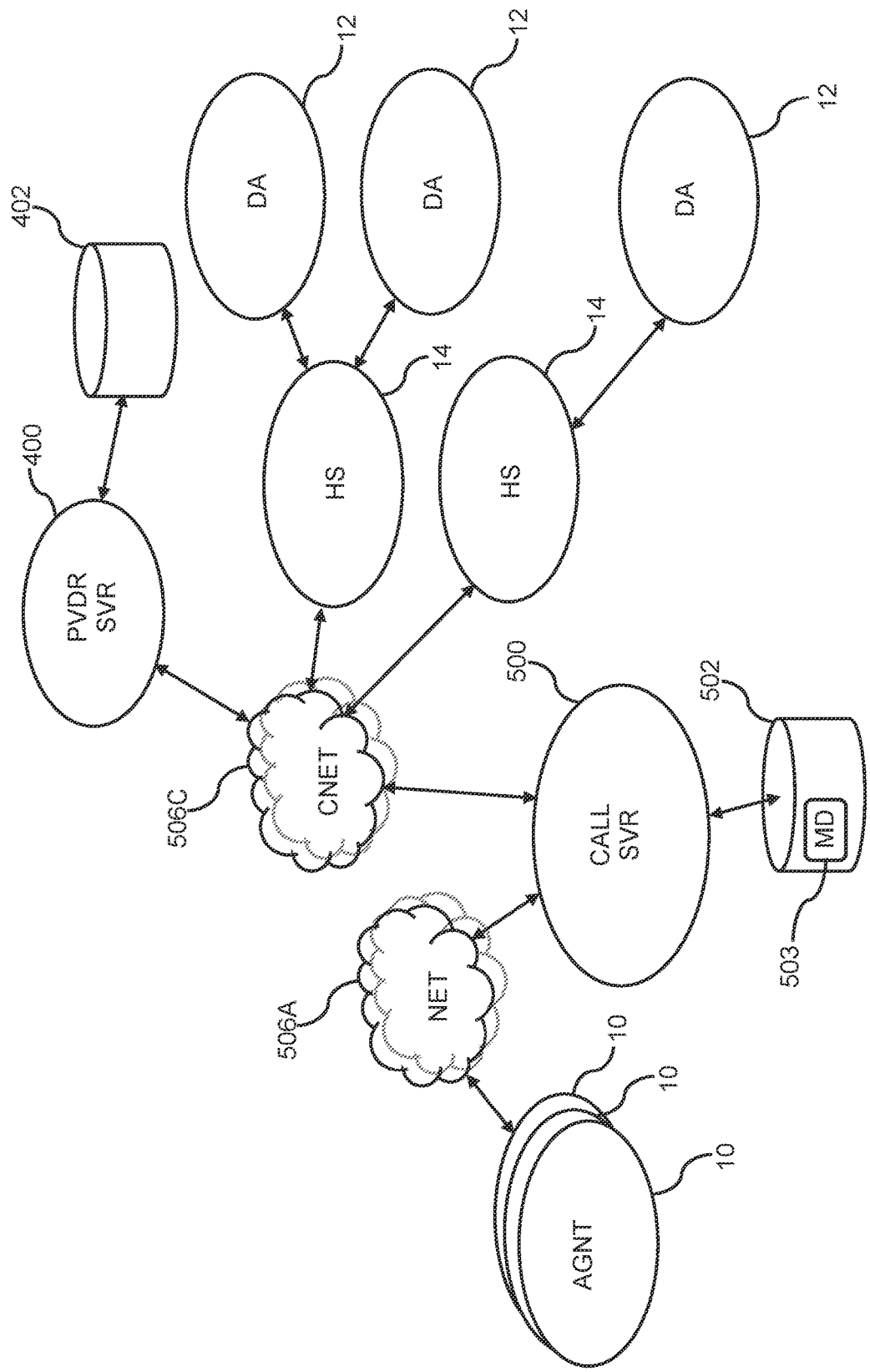
FIGS. 2 and 2A illustrate alternate data connection diagrams of system for providing help.
Figure 2A:
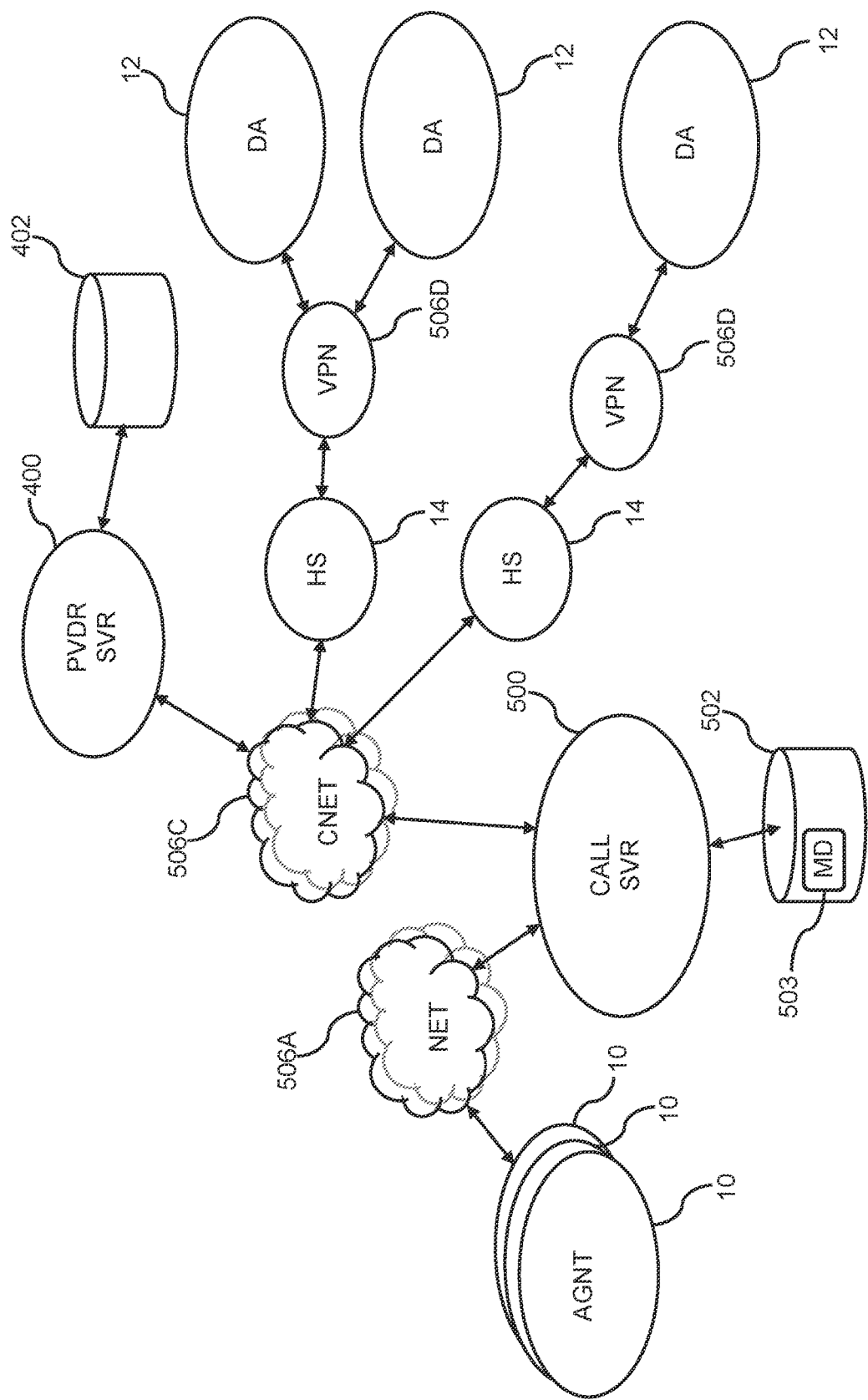

Referring to FIGS. 2 and 2A, data connection diagrams of the exemplary system for providing help using mobile hotspots 14 which are part of the centrally programmed and managed system are shown. In this example, agent computers 10 (e.g., personal computers) communicate (as in FIG. 1) through a first network 506A (e.g. the Internet, local area network, etc.) to a call center server computer 500. Although one path between the agent computers 10 and the call center server computer 500 is through the first network 506A as shown, though any known data path is anticipated. For example, a local area network, Wi-Fi combined with a wide area network, which includes the Internet.

To totally alleviate the need for an installer, the configuration of FIG. 2A includes a virtual private network repeater 506D that is preconfigured to communicate with one or more of the digital assistants 12 that are provided at the time of purchase or additional digital assistants that are later programmed with security codes to access the virtual private network repeater 506D. The virtual private network repeater 506D plugs directly into the mobile hotspots 14, for example, using a provided Ethernet cable. In this way, the individual in need simply unpacks the virtual private network repeater 506D, mobile hotspot 14, and digital assistant(s) 12, connects power to such, and plugs the provided cable into the mobile hotspots 14 and not administration need be performed in the home. Not only are the digital assistants 12 pre-programmed to communicate directly to the virtual private network repeater 506D over wireless connections using pre-programmed credentials of which there is no need for the individual in need to know or understand, each digital assistant 12 is protected by the virtual private network repeater 506D by enhanced encryption and firewall protection. Therefore, even if any other existing wireless routers within the facility/home are poorly installed (e.g. with weak encryption, simple passwords, lack of firewall protection), the digital assistants 12 are virtualized by the virtual private network repeater 506D, protecting confidential medical information that may be shared between the agents at the agent computers 10 and the individual serviced by the digital assistants 12. This being said, the individuals serviced by the digital assistants 12 are still free to use any other feature of the digital assistants 12 (e.g. asking the time or weather or playing music).

Although any number of digital assistants 12 is anticipated, three are shown for brevity reasons. The digital assistants 12 monitor sound and analyze the sound for specific utterances. Of interest to the system for providing help is specific utterances that are configured to request help such as "Alexa, Call for help," or similar. In the embodiment shown in FIG. 2, two of the digital assistants connect to a first one of the mobile hotspots 14 and a single other of the digital assistants connects to a second of the mobile hotspots 14. It is anticipated that in a smaller location (e.g. home or office), a single mobile hotspot 14 is sufficient to provide connectivity to all digital assistants 12 within that location (including a single digital assistant 12), while in larger locations more than one mobile hotspot 14, connected as a repeater using the same SSID and access code, may be required to provide adequate local wireless coverage.

Each mobile hotspot 14 communicates through the cellular network 506C to the call center server computer 500, typically when and after the specific utterances that request help are detected.

In the embodiment shown in FIG. 2A, two of the digital assistants connect to a first one of the mobile hotspots 14 through a first virtual private network repeater 506D and the other of the digital assistants 12 connects to a second of the mobile hotspots 14 through a second virtual private network repeater 506D. It is anticipated that in a smaller location (e.g. home or office), a single mobile hotspot 14 is sufficient to provide connectivity to all digital assistants 12 within that location (including a single digital assistant 12), while in larger locations more than one mobile hotspot 14, in some embodiments connected as a repeater using the same SSID and access code, may be required to provide adequate local wireless coverage.

Figure 3:
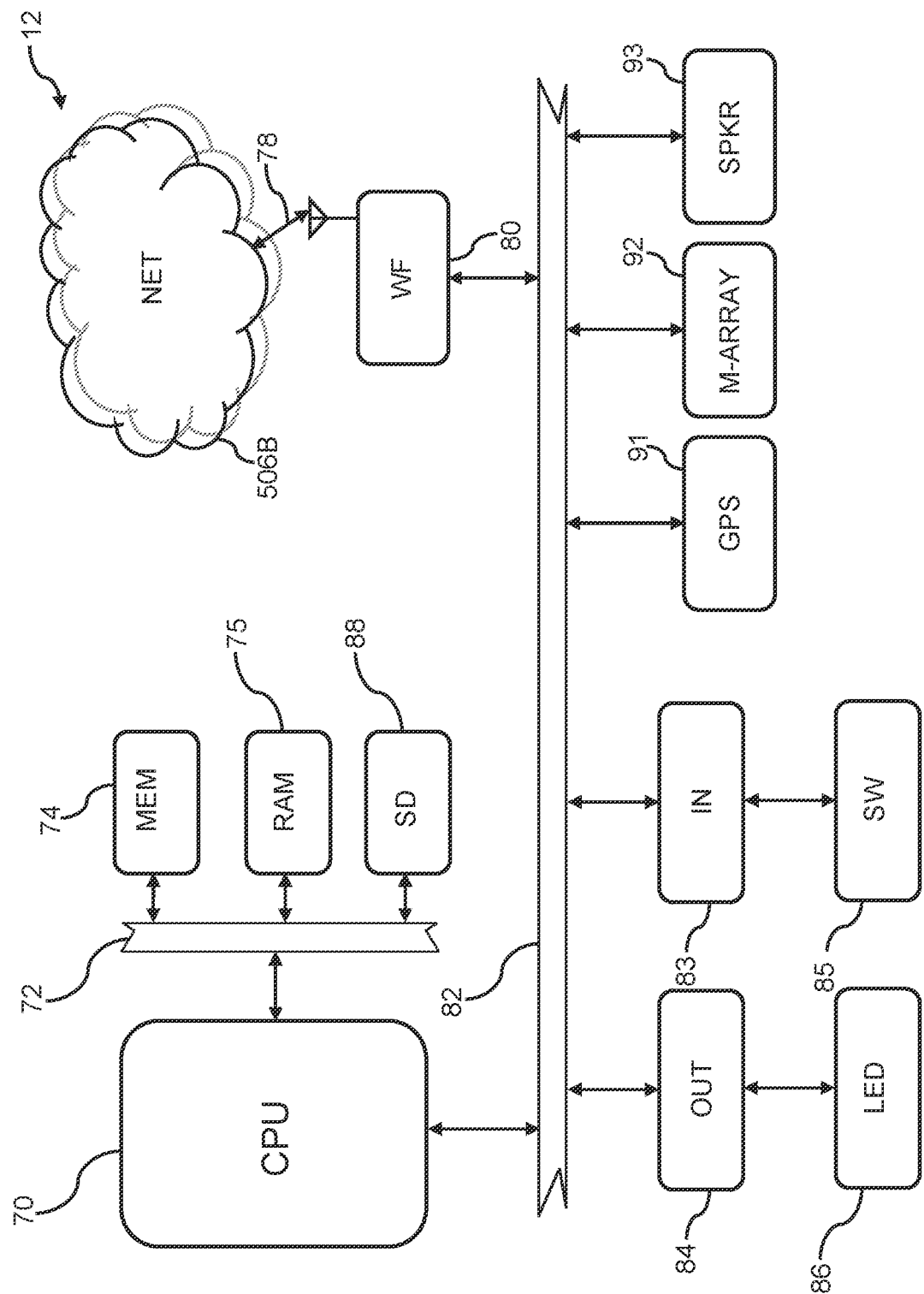
FIG. 3 illustrates a schematic view of a digital assistant of the system for providing help.

Referring to FIG. 3, a schematic view of an exemplary digital assistant 12 is shown as used as an end-point device in the system for providing help. The exemplary digital assistant 12 is a processor-based device for providing voice recognition and command execution. The present invention is in no way limited to any particular digital assistant 12 and many other devices are anticipated that offer similar voice recognition and command execution. Such other processor-based devices that are equally anticipated include, but are not limited to, Google® Assistant series of smart speaker digital assistants, Apple's® Siri® series of smart speaker digital assistants, other smart speakers which have embodied a similar or licensed artificial intelligence powered digital assistant of any type, smart phones, cellular phones, thermostats, fitness devices, etc.

The exemplary digital assistant 12 represents a typical device used for accessing user interfaces of the system for providing help. This exemplary digital assistant 12 is shown in its simplest form. Different architectures are known that accomplish similar results in a similar fashion, and the present invention is not limited in any way to any particular system architecture or implementation. In this exemplary digital assistant 12, a processor 70 executes or runs programs in a random-access memory 75. The programs are generally stored within a persistent memory 74 and loaded into the random-access memory 75 when needed. In some digital assistants 12, a removable storage 88 (e.g., compact flash, SD) offers removable persistent storage. The processor 70 is any processor, typically a processor designed for phones. The persistent memory 74, random-access memory 75, and removable storage slot are connected to the processor by, for example, a memory bus 72. The random-access memory 75 is any memory suitable for connection and operation with the selected processor 70, such as SRAM, DRAM, SDRAM, RDRAM, DDR, DDR-2, etc. The persistent memory 74 is any type, configuration, capacity of memory suitable for persistently storing data, for example, flash memory, read only memory, battery-backed memory, etc. In some agent computers 10, the persistent memory 74 is removable, in the form of a memory card of appropriate format such as SD (secure digital) cards, micro SD cards, compact flash, etc.

Also connected to the processor 70 is a system bus 82 for connecting to peripheral subsystems such as a wireless network interface 80 (e.g. Wi-Fi), an output port 84 for driving indicators 86, and an input port 83 for reading switch inputs 85, though there is no restriction on inputs and outputs.

In general, some portion of the persistent memory 74 and/or the removable storage 88 is used to store programs, executable code, and data, etc.

The peripherals are examples, and other devices are known in the industry such as Global Positioning Subsystems 91, the details of which are not shown for brevity and clarity reasons.

The wireless network interface 80 connects the exemplary digital assistant 12 to the second network 506B or cellular network 506C through any known or future protocol such as Ethernet, WI-FI, GSM, TDMA, LTE, etc., through a wired or wireless medium 78. There is no limitation on the type of connection used. The wireless network interface 80 provides data and messaging connections between the exemplary digital assistant 12 and the call center server computer 500 through the second network 506B.

For receiving voice commands from a user, the digital assistant 12 has an audio input device such as a microphone or microphone array 92.

For providing responses and information, the digital assistant 12 has a transducer device or speaker 93.

Figure 4:
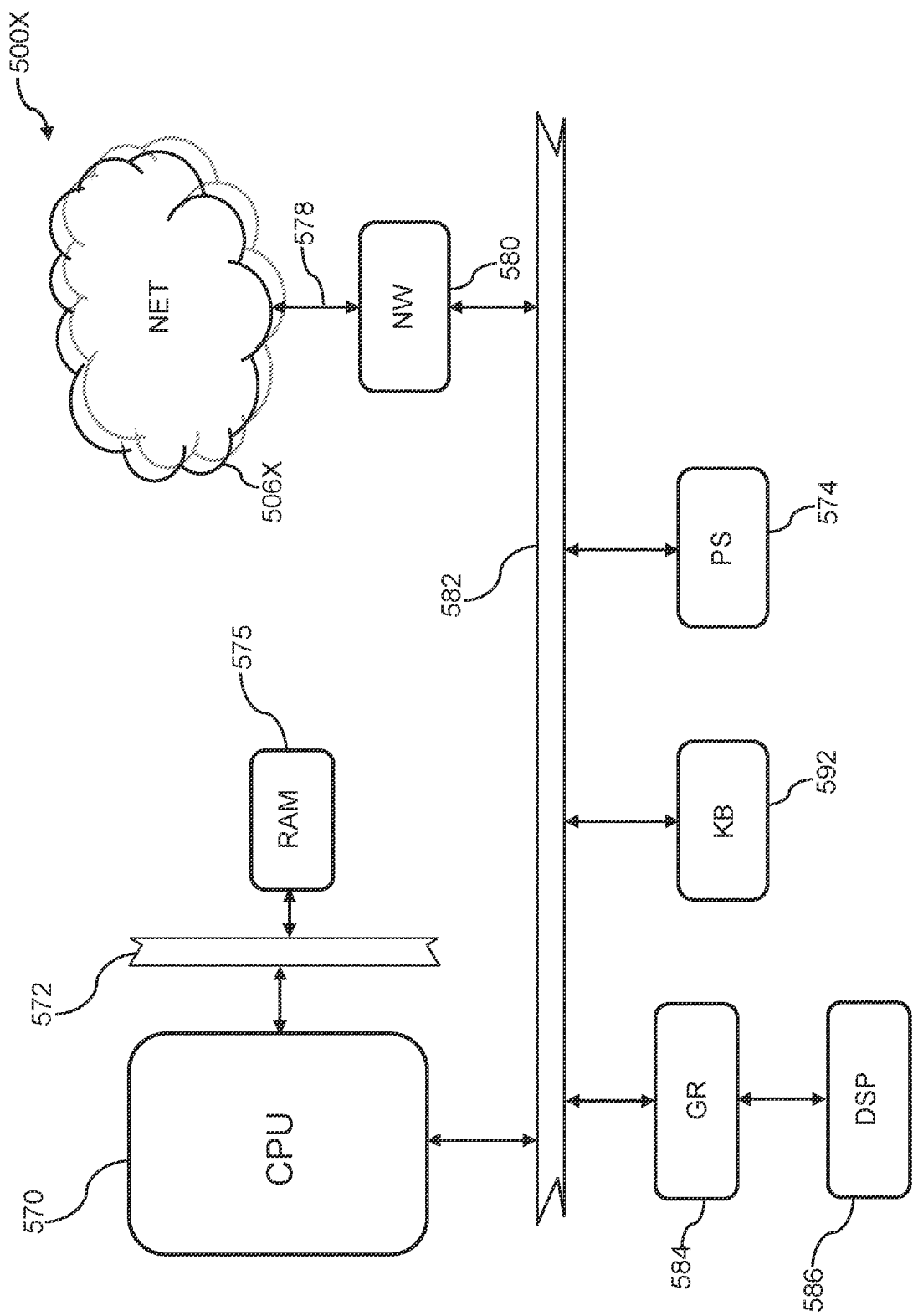
FIG. 4 illustrates a schematic view of a typical computer system.

Referring to FIG. 4, a schematic view of a typical server computer system 500X (e.g., call center server computer 500) is shown. The example server computer system represents a typical server computer system 500X used as in the system for remote computer control. This exemplary server computer system 500X is shown in its simplest form. Different architectures are known that accomplish similar results in a similar fashion and the present invention is not limited in any way to any particular computer system architecture or implementation. In this exemplary server computer system 500X, a processor 570 executes or runs programs in a random-access memory 575. The programs are generally stored within a persistent memory 574 and loaded into the random-access memory 575 when needed. The processor 570 is any processor, typically a processor designed for computer systems with any number of core processing elements, etc. The random-access memory 575 is connected to the processor by, for example, a memory bus 572. The random-access memory 575 is any memory suitable for connection and operation with the selected processor 570, such as SRAM, DRAM, SDRAM, RDRAM, DDR, DDR-2, etc. The persistent memory 574 is any type, configuration, capacity of memory suitable for persistently storing data, for example, magnetic storage, flash memory, read only memory, battery-backed memory, magnetic memory, etc. The persistent memory 574 is typically interfaced to the processor 570 through a system bus 582, or any other interface as known in the industry.

Also shown connected to the system bus 582 is a network interface 580 (e.g., for connecting to a data network 506X— e.g. first network 506A and/or second network 506B and/or cellular network 506C), a graphics adapter 584 and a keyboard interface 592 (e.g., Universal Serial Bus-USB). The graphics adapter 584 receives information from the processor 570 and controls what is depicted on a display 586. The keyboard interface 592 provides navigation, data entry, and selection features.

In general, some portion of the persistent memory 574 is used to store programs, executable code, data, contacts, and other data, etc.

The peripherals are examples and other devices are known in the industry such as pointing devices, touch-screen interfaces, speakers, microphones, USB interfaces, Bluetooth transceivers, Wi-Fi transceivers, image sensors, temperature sensors, etc., the details of which are not shown for brevity and clarity reasons.

Figure 5:
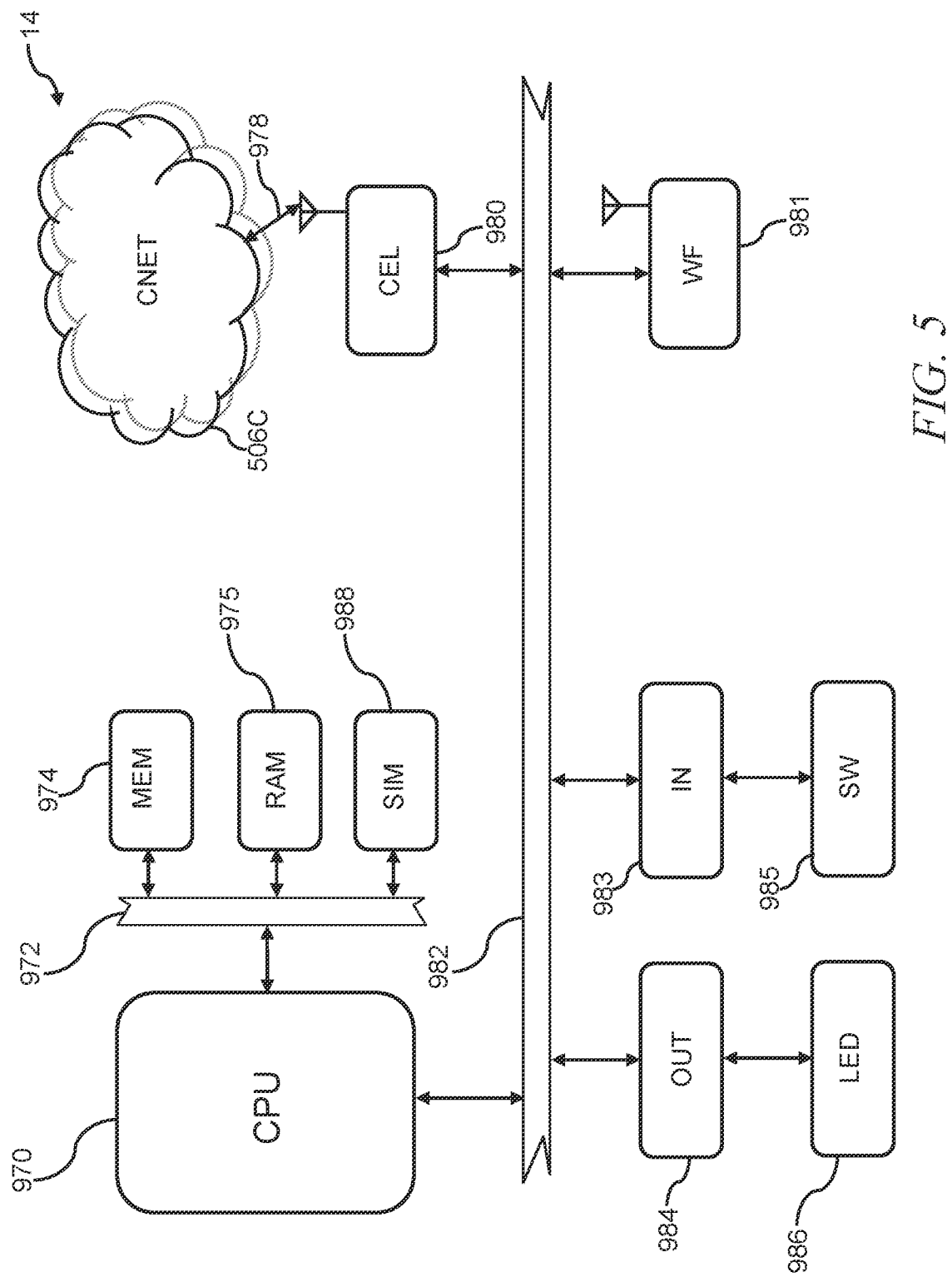
FIG. 5 illustrates a schematic view of a typical hotspot.

Referring to FIG. 5, a schematic view of an exemplary mobile hotspot 14 is shown as used in the system for providing help. The exemplary mobile hotspot 14 is a processor-based device for providing data connectivity through the cellular network 506C. The present invention is in no way limited to any particular mobile hotspot 14 and many other devices are anticipated that offer similar connectivity.

The exemplary mobile hotspot 14 represents a typical device used for providing data connectivity using the cellular network 506C (any cellular data network is anticipated including, but not limited to, CDMA, GSM, TDMA, LTE, etc. This exemplary mobile hotspot 14 is shown in its simplest form. Different architectures are known that accomplish similar results in a similar fashion, and the present invention is not limited in any way to any particular system architecture or implementation. In this exemplary mobile hotspot 14, a processor 970 executes or runs programs in a random-access memory 975. The programs are generally stored within a persistent memory 974 and loaded into the random-access memory 975 when executed. A subscriber identity module 988 (SIM or SIM card) securely stores an international mobile subscriber identity (IMSI) number and its related key, which are used to identify and authenticate subscribers on the cellular network 506C. The processor 970 is any processor, typically a processor designed for data communications. The persistent memory 974, random-access memory 975, and subscriber identity module 988 are connected to the processor by, for example, a memory bus 972. The random-access memory 975 is any memory suitable for connection and operation with the selected processor 970, such as SRAM, DRAM, SDRAM, RDRAM, DDR, DDR-2, etc. The persistent memory 974 is any type, configuration, capacity of memory suitable for persistently storing data, for example, flash memory, read only memory, battery-backed memory, etc.

Also connected to the processor 970 is a system bus 982 for connecting to peripheral subsystems such as a cellular network interface 980 (e.g. cellular interface) and a local wireless network interface 981 (e.g. Wi-Fi). In some embodiments, an output port 984 is provided for driving indicators 986, and an input port 983 is provided for reading switch inputs 985, though there is no restriction on inputs and outputs.

In general, some portion of the persistent memory 974 is used to store programs, executable code, and data, etc.

The peripherals are examples, and other devices are known in the industry are anticipated, the details of which are not shown for brevity and clarity reasons.

The cellular network interface 980 connects the mobile hotspot 14 to the cellular network 506C through any known or future protocol such as GSM, TDMA, LTE, etc. There is no limitation on the type of cellular connection used. The cellular network interface 980 provides data and messaging between the exemplary mobile hotspot 14 and the cellular network 506C.

The local wireless network interface 981 connects the mobile hotspot 14 to a local wireless network through any known or future protocol such as Wi-Fi (802.11x), Bluetooth, etc. There is no limitation on the type of local wireless connection used. The local wireless network interface 981 provides data and messaging between the mobile hotspot 14 and the digital assistants 12.

Figure 6:
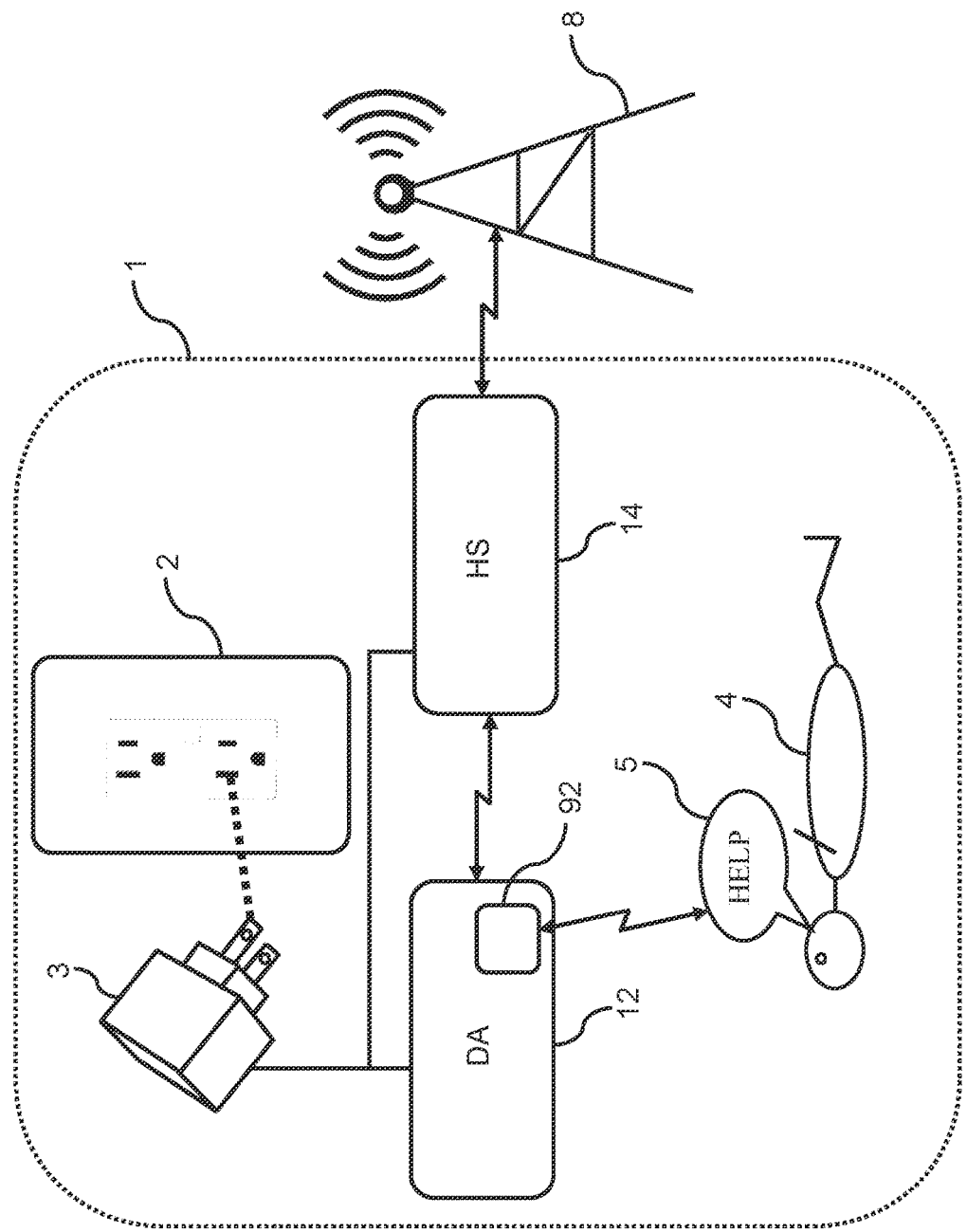
FIGS. 6 and 6A illustrate views of typical home configurations.
Figure 6A:
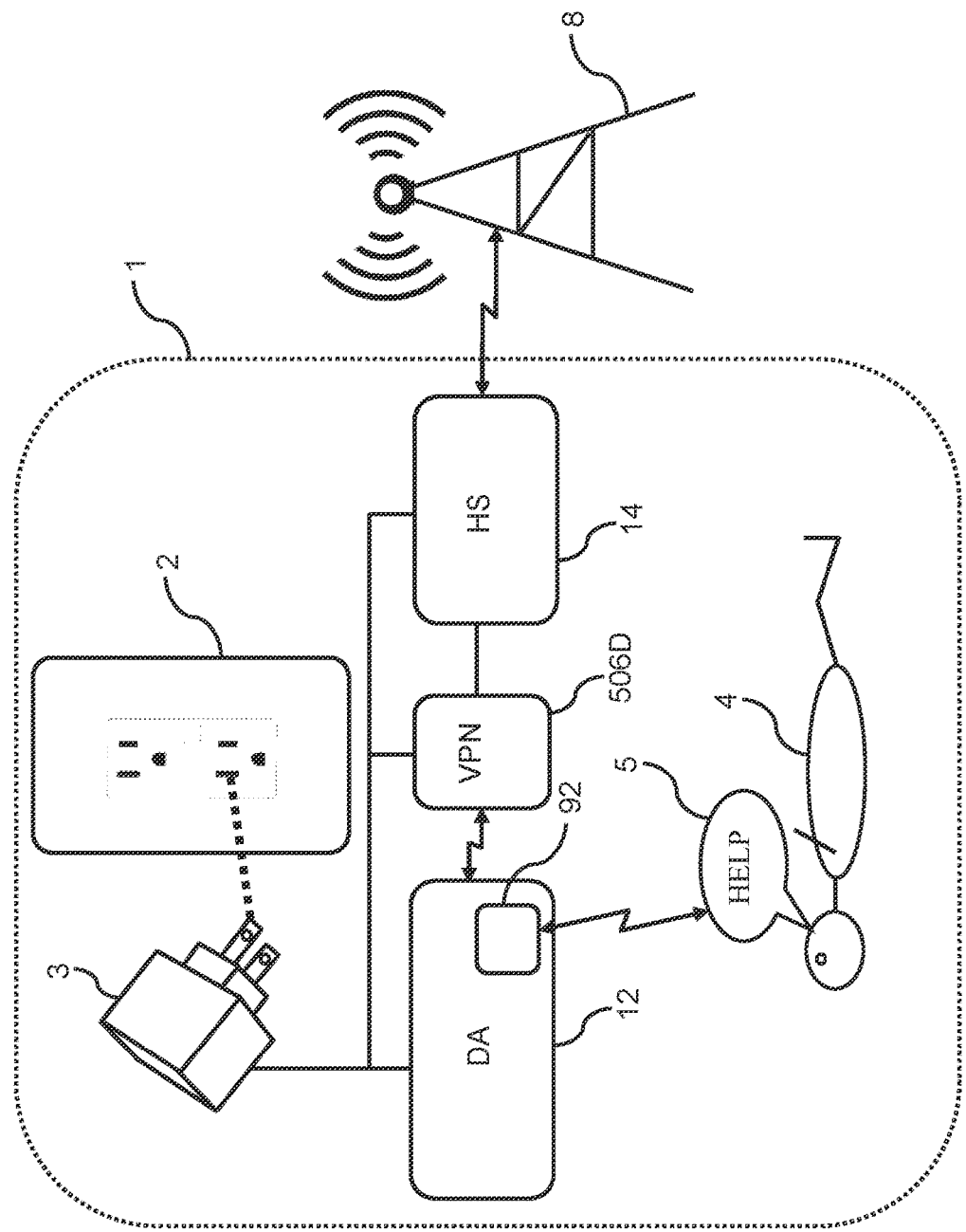

Referring to FIGS. 6 and 6A, views of a typical turn-key, home configuration are shown. Within the home 1 (or office or any area), a digital assistant 12 is powered, for example, by a wall transformer 3 plugged into a standard AC outlet 2. The digital assistant 12 communicates wirelessly (e.g. by Wi-Fi) with a mobile hotspot 14, shown in this example as being powered by the same wall transformer 3. It is anticipated that the components within the home 1 of FIG. 6 (except the standard AC outlet 2) be provided as a turn-key solution, each pre-configured to function properly with each other.

The mobile hotspot 14 communicates with the call center server computer system 500 through a wide area wireless network such as a cellular network 506C (a single cell tower 8 is shown as a representation of such).

In this example, a user 4 has fallen and utters the preprogrammed specific utterance 5 (e.g., "Alexa, Call for help" or similar). that is received by the microphone array 92 of the digital assistant 12. The digital assistant 12, recognizing the utterance as the preprogrammed specific utterance 5 communicates with the mobile hotspot 14 (e.g. via Wi-Fi). After receiving the communication, the mobile hotspot 14 contacts the call center server computer system 500 through the cellular network 506C (and/or any other networks) as represented by the cell tower 8.

In some embodiments, the call center server computer system 500 assigns an agent computer 10 and associated call center agent, connecting to that agent computer 10 and displaying information related to the user 4, by associating the caller ID number associated with the smart speaker system to the database of the provider centrally managed system, so that the agent is able to identify the name and exact location of the caller, and is able to understand the issue and determine the extent of the emergency, should an emergency exist.

In some embodiments, the agent computer 10 is placed in voice communication with the digital assistant 12 and, as the agent speaks, digitized speech is sent from the agent computer 10 to the digital assistant 12 and the user 4 hears what the agent is saying through one or more speakers 93 of the digital assistant 12. Likewise, when the user 4 speaks, digitized speech is sent from the digital assistant 12 to the agent computer 10 and the agent hears what the user 4 is saying through one or more speakers of agent computer 10. In this way, the agent is capable of determining the identity of the caller from the centrally managed database, and determine the extent of the emergency and able to determine what course of action is needed, for example, verbal help, sending private responders (e.g. at an assisted living location), contacting an emergency response resource (e.g. calling 911 in the USA), etc.

As many users 4 that may need emergency help often lack technical skills, those users 4 that are in greatest need of the system for providing help, it is desired to provide a "turnkey" system for providing help, in that, the user 4 need not be concerned with configuring wireless networks, home internet services, phone services, smartphone app downloading, and programming a digital assistant etc. The desire is that the user 4 only need to plug in the system for providing help to a wall power outlet and the system for providing help self-configures and operates. As many users 4 have no wireless internet access, one such pre-configuration includes one or more digital assistants 12 and one or more mobile hotspots 14, pre-configured to communicate with each other to provide services of the system for providing help (in addition to other services available from the digital assistant 12 such as answering questions, playing music, etc.). In this, the digital assistant(s) 12 is/are pre-configured to connect with the mobile hotspot(s) 14, the digital assistant(s) 12 is/are preprogrammed with the pre-programmed specific utterance 5, and the digital assistant(s) 12 have a private identity 102 (see FIG. 7) that is unique and known to the call center server computer system 500 based on the proprietary centrally managed program database. By having a private identity 102 such as 1112223333@gmail.com, the digital assistant(s) 12 do not disclose the identity of the user 4 in outside communications unless the user 4 explicitly discloses such information. Therefore, until an emergency is determined, the agent might only be provided with a first name of the user 4 for polite addressing, thereby not releasing any private information until it is determined that an emergency exists. Such identity hiding is important for HIPAA compliance.

Note that many available digital assistants 12 have a wake-up work such as "Alexa," and such has been included in the preprogrammed specific utterance 5, for example, "Alexa, Call for help." The main reason is that should someone on the radio or television say, "send help," the system for providing help need not interpret this as an emergency.

When it is determined that an emergency exists, the private identity 102 is used by the call center server computer system 500 to access user records (e.g. from data storage 502) to determine the name, phone number, and location of the user 4; history of this user's 4 issues; medical information 503 regarding the user 4 (e.g. heart conditions, medications, mobility); local support staff locations and contact information (e.g. roaming staff, staff in assisted living); etc.

Although it is preferred to use a digital assistant 12 as a portal into the system for providing help, parallel systems are also anticipated including by phone in which the DNIS (Dialed Number Identification System) or caller ID methodology is used to determine the identity of the user, by matching the DNIS (caller ID) with the proprietary centrally managed system database, or through programming one or more phone numbers of the system for providing help into a user's smart phone.

After installation and configuration, the user 4 typically makes an initial test call using system, by saying the preprogrammed specific utterance 5, for example: "Alexa, Call For Help" or similar. Note that in this preprogrammed specific utterance 5, the first word, "Alexa," wakes up the digital assistant 12; the second word, "Call," is a command to instruct the digital assistant 12 to initiate a digital call; and the remaining words, "for help" identify the called party, which is that of a monitored security number (e.g. the call center server computer system 500).

The system for providing help maintains a monitoring center (UL approved) with trained operators preferably providing continual operation with redundant back up. The system for providing help maintains an account for each user 4, with their address, emergency contacts such as neighbors, friends, family and physicians contact numbers, and a limited medical history and specialized instructions (Protected Medical Information or "PHI"). In some embodiments, the system for providing help offers additional services and solutions to maintain contact with a user 4 on a daily basis, verify their wellbeing and operation of their digital assistant(s) 12. By removing a need for any industry standard PERS base station (which may broadcast a customer account identification number) or a PERS (mobile cellular pendant or wrist band) improved security and privacy is provided. When a phone or smartphone is used to access the system for providing help, the DNIS (Dialed Number Identification System) or Caller ID is used as a unique index into account information from a database each time a call is received from a registered user.

If a user 4 desires a body-worn device (not shown for brevity and clarity) such as a personal panic button, a pendant or a wrist band, it is anticipated that the digital assistant 12 and/or mobile hotspot 14 be configured to interface with the body-worn device and initiate an interaction with the call center server computer system 500. An agent of the system for providing help, interfaced to the call center server computer system 500, determines if the user 4 needs assistance, and, if so, summons assistance by contacting friends, neighbors or family who can help; or an ambulance if needed, fire rescue if needed, police if needed or other emergency response as warranted.

In FIG. 6A, the mobile hotspot 14 is connected to a virtual private network repeater 506D and the virtual private network repeater 506D communicates wirelessly to the one or more digital assistants 12.

Figure 7:
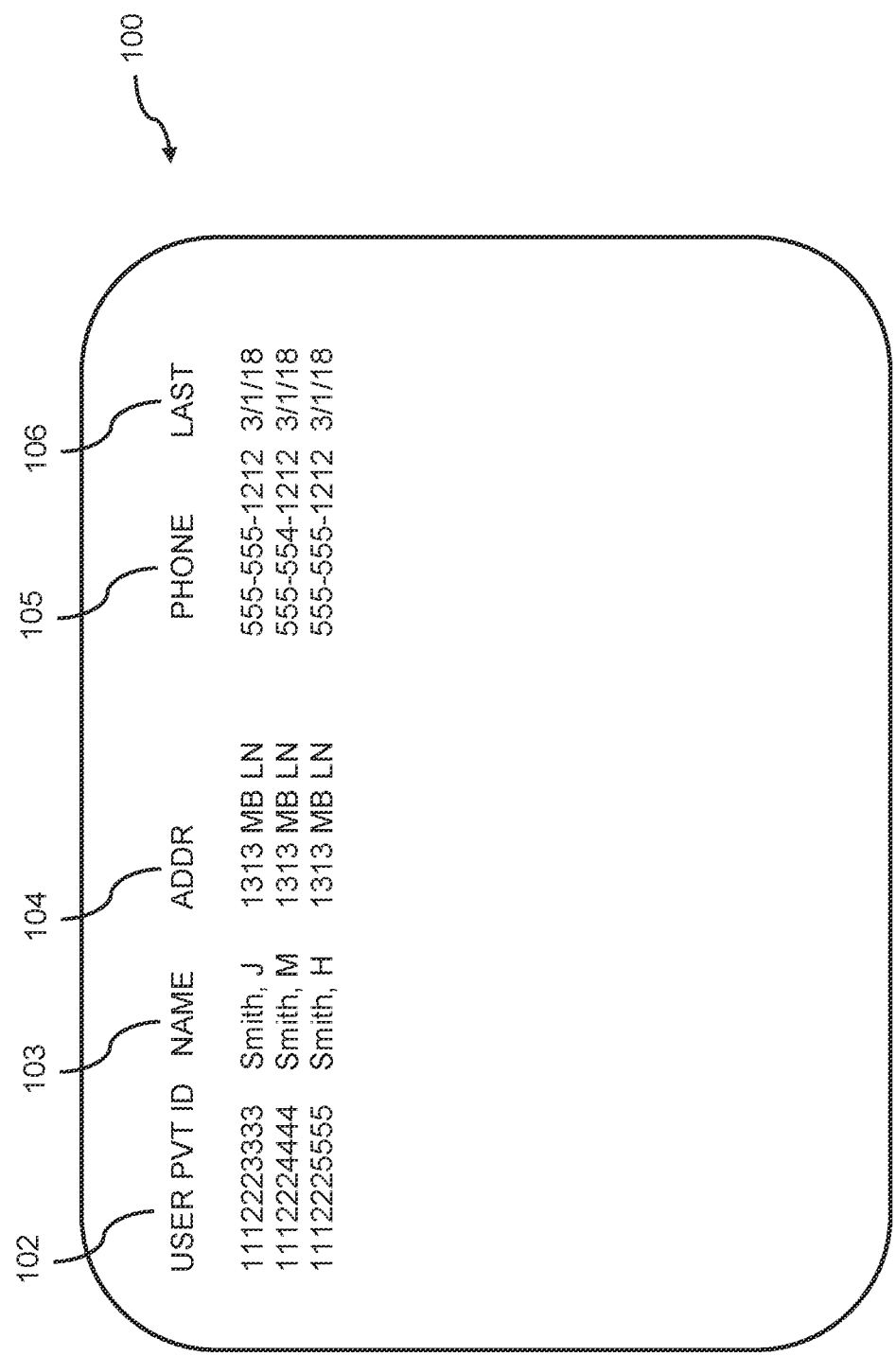

Referring to FIGS. 7, 8, 9, and 10, exemplary user databases 100 are shown. In FIG. 7, each user 4 has a private identity 102 that is unique. When a request is received by the call center server computer system 500, the call is assigned to one of the agent computers 10 and an agent associated with that agent computer 10. As needed and allowed under privacy laws for PHI (HIPAA), the agent is provided other information regarding the user 4 who has made the request, including the name 103 of the user 4, the address 104 of the user 4, the phone number 105 of the user 4, and a date of the last request/call 106 made by the user 4.

Figure 8:
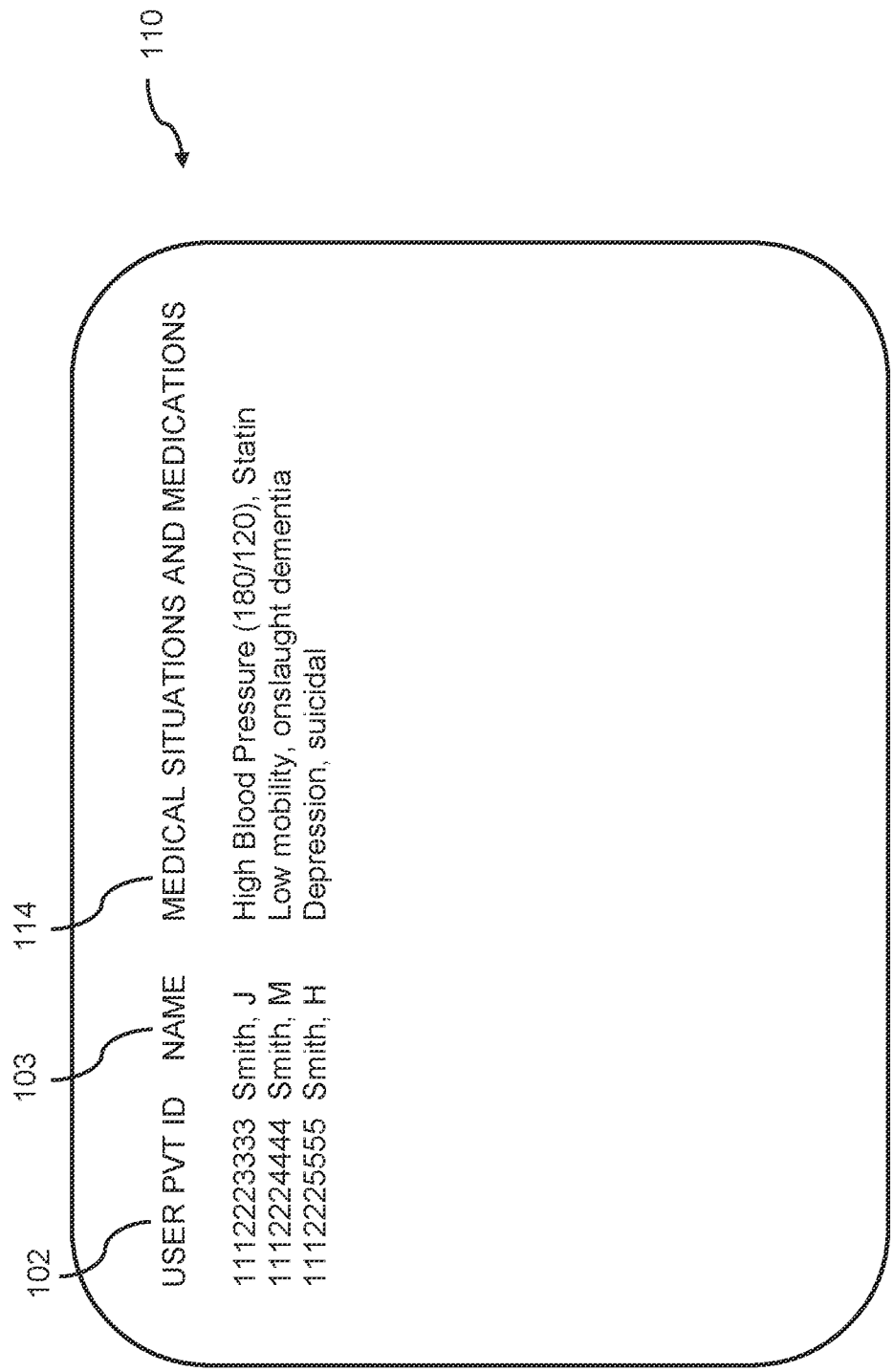
Figure 10A:
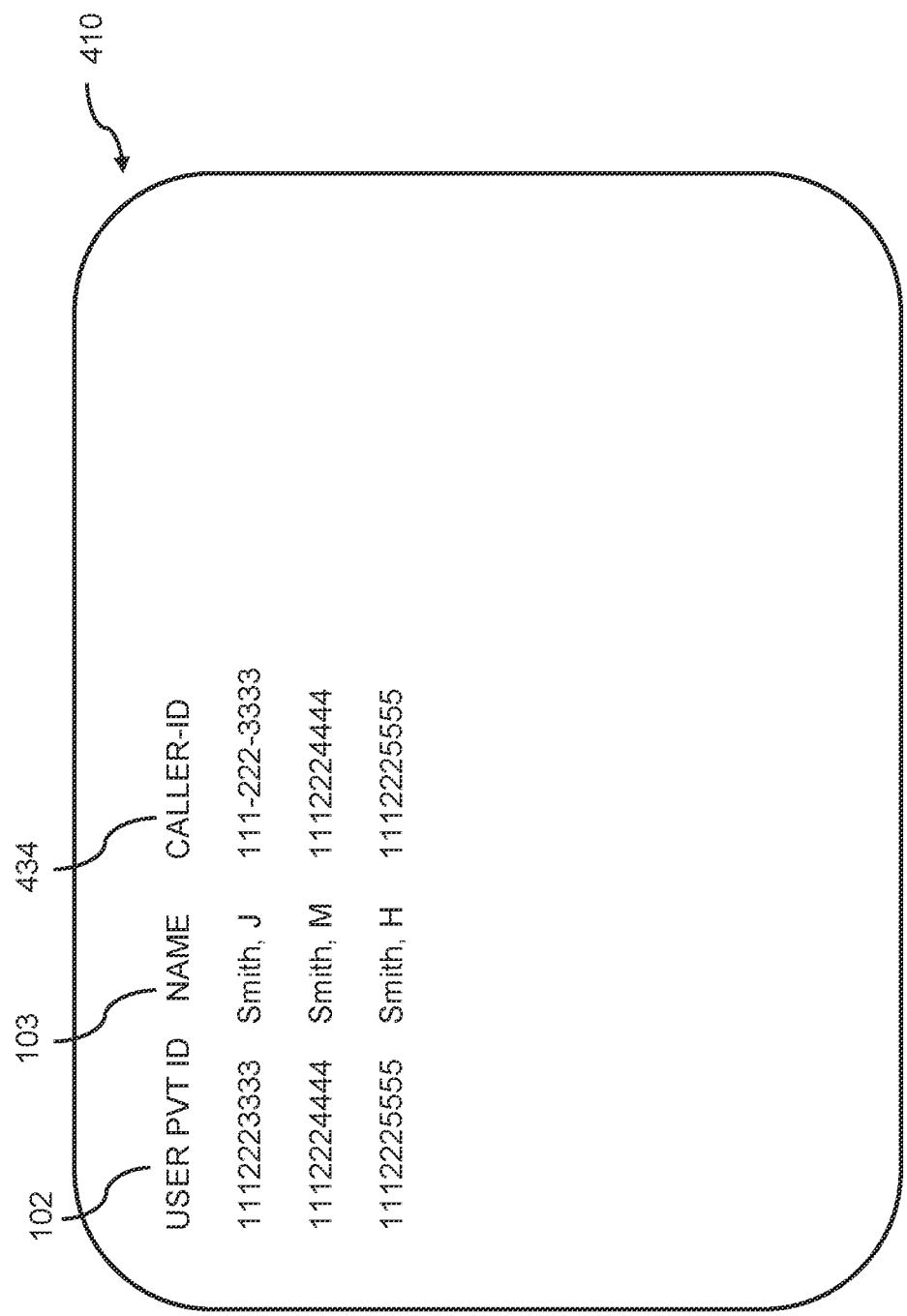
FIG. 10A illustrates an exemplary digital assistant provider database.

When it is determined that an emergency exists, the private identity 102 is used by the call center server computer system 500 to access user records (e.g. from data storage 502) to determine the name, phone number, and location of the user 4. If the agent requires further information and such is needed and allowed under privacy laws, the agent gains access to medical information 114 regarding the user 4 (e.g. heart conditions, medications, mobility) as shown in FIG. 8, indexed by the private identity 102. If the agent needs further information regarding prior requests/calls and such is needed and allowed under privacy laws, the agent gains access to a history 124 of the user 4 which includes, for example, history of prior calls or other related information such as important medical events and diagnosis (e.g. hip replacement, knee scope operation, diagnosed with cancer).

If it is determined that the user 4 needs help, there is contact information 134 as shown in FIG. 10. The contact information 134 includes, for example, global contacts, local contacts, and personal contacts that are made available to the agent. Global contacts such as E911 are less effective in a distributed environment, as it is anticipated that the agent is not in the same location as the user 4, and therefore, dialing of 911 or emergency first responders by the agent will not solicit help at the location of the user 4. Local contacts as shown in FIG. 10 provide contact information (e.g. phone numbers) for emergency services that are local to the user 4 (e.g. in the same town, zip code, etc.). Local contacts also include local support staff at the location of the user 4 (e.g. roaming staff, staff in assisted living). Personal contacts (as shown in FIG. 10) include contacts of care givers and loved ones specific to the user 4 (e.g. family members, clergy, and neighbors). Note that the contact information 134 includes any way known to contact another including, but not limited to, phone numbers, addresses, email addresses, social media addresses, voice-over-IP addresses, Ai powered digital assistants (Alexa to Alexa messaging or calling or similar), etc.

In some embodiments, the private identity 102 is, or is part of, an email address, as some digital assistants 12 require an email address at registration and, most digital assistants 12 allow for multiple digital assistants 12 to be associated with a single email address used in creating the centrally managed system. Therefore, although the private identity 102 of the users 4 is shown as a 10 digit number, it is anticipated that, in some embodiments, the private identity 102 is an email address such as 1112223333@gmail.com or 1112223333@aol.com or an alpha-numeric combination such as CC1112223333, etc.

In some embodiments, the private identity 102 is, or is part of, a phone number, as some digital assistants 12 require a phone number be provided at registration and, most digital assistants 12 allow for multiple digital assistants 12 to be associated with a phone number that is used in creating a provider account used by the service provider's server 400. Therefore, although the private identity 102 of the users 4 is shown as a 10 digit number, it is anticipated that, in some embodiments, the private identity 102 is phone number such as 1112223333 or 1112223333 etc. In such, when the specific utterance 5 (e.g. "Alexa, Call for help") is detected by the digital assistant 12, the digital assistant 12 contacts the service provider's server 400 to make the call to a contact, in this example, "for help." The phone number associated with "for help" in the user's 4 contact list is the phone number of the service and the call is made by the service provider's server 400 to the call center server computer system 500. The service provider's server 400 accesses the provider account 410 of the user from the provider's database 402 (see FIG. 10A). The call server then calls the call center server computer system 500 with the caller-id 434 from the provider account 410. The call center server computer system 500 then uses the caller-id 434 to recognize which user 4 is associated with this incoming call. Note that the provider account 410 is abbreviated for clarity reasons.

Configuration and installation of one or more digital assistants 12 in a home is a daunting task, even for the technical literate. Many intended users of the system for providing help are low on the technical literacy scale or have an ailment/disability that makes it almost impossible to setup, configure, and install the digital assistants 12 in their facility (e.g. home). Further, many users 4 live in locations where there is no wireless local area network coverage (e.g. Wi-Fi), further requiring each user 4 to arrange Internet access and a wireless local area network coverage, for example, from a cable or fiber optic provider.

Now, assuming the user 4 arranges for installation of Internet access as well as a wireless local area network within their facility, the user 4 must activate "Phone Skills" for the digital assistant 12 and/or update a contact list to include a contact that connects with the call server. For example, if the phone skills for the digital assistant 12 require the initiation word, "call", the preprogrammed specific utterance 5 will start with "Alexa, call" or "Hey XX, call." Now the user 4 associates the remainder of the preprogrammed specific utterance 5 with an address/phone-number of the call center server computer system 500. For example, the user adds a contact of "for help" in their address book and provides the phone number (or IP address) of the call center server computer system 500 as the primary contact for this contact. Therefore, the preprogrammed specific utterance 5 is, for example, "Alexa, call for help," or "Hey XX, call for help." Now the user 4 must try to initiate a request for help by saying, for example, "Alexa, call for help," or "Hey XX, call for help," and if an agent answers, they are all set. Simple? Not really. Further, the above provides for a one-way initiation of connectivity—from the digital assistant (s) 12 of the user to the call center server computer system 500. There is no way for the call center server computer system 500 to initiate contact with any equipment (e.g. Internet infrastructure and digital assistant(s) 12 within the facility of the user 4). In some embodiments, it is important to provide "heartbeat" monitoring of the digital assistant(s) 12, as should a digital assistants 12 fail, some subset of the users 4 will not know about the failure until it is too late as some users will not use their digital assistant(s) 12 for any other purpose other than requesting help.

Although examples of the preprogrammed specific utterance 5 have been in English with a known wake-up word, for example, "Alexa, call for help," or "Hey XX, call for help," it is fully anticipated that other languages as well as custom wake-up words will be deployed. Note that because the digital assistant 12 is typically listening for utterances all day long, it is wise to use a wake-up word that is uncommon. For example, if the preprogrammed specific utterance 5 is simplified to "Get Help," false alarms might arise when watching television and an actor on the television says, "Get Help."

Some users 4 are capable if executing the steps of installing and configuring of one or more digital assistants 12. For users 4 that are not capable or desire improved coverage, a preprogrammed system is provided upon purchase or activation of a service agreement with the monitoring company. The preprogrammed system is ready to use upon activation by a user simply plugging the digital assistants 12 into an available power outlet.

It is also anticipated that the system for requesting help be implemented using a smartphone instead of or in addition to a digital assistant 12, as voice recognition is often included in many android, Microsoft® and Apple® smartphones. Three limitations are present with smartphones is that: they require recharging, in some instances must be woken by a physical activity (e.g. pressing a wake button) and most users 4 will not want to deploy a plugged-in cellphone in each room of the facility (e.g. home). Further, as each will be a fully functional smartphone, cellular providers might not offer low-cost plans for emergency use only.

To use the system for requesting help an emergency, such as the onset of symptoms of a serious illness (chest pains in the case of a heart-attack) or other, the user 4 says the preprogrammed specific utterance 5, for example, "Alexa, call for help," or "Hey XX, call for help," loudly and clearly once. In a preferred embodiment, the digital assistant 12 will respond, "Calling for Help Now". The request will be received by the call center server computer system 500 and the request will be forwarded to one of the agent computer 10 along with information of the user's 4 name and location from the centrally managed system database. A two-way voice connection is made between the agent computer 10 and the digital assistant 12 that requested help (and, in some embodiments, with other digital assistants 12 with the same facility). As an example, the agent at the agent computer 10 will ask the nature of the emergency. If the user 4 is unable to speak further, perhaps incapacitation due to the emergency or illness, the security call center detects that you made the request for help and, if unable to gain a response, will either call E911 or local emergency first responders directly with your emergency or follow other agreed upon protocol for this user 4 (as per their account) such as contacting a private duty help agent (e.g. a roaming agent local to the user 4), assisted living staff, neighbors, etc.

In some cases, the user has fallen and is having trouble getting back up on their bed or chair etc. in this case, the user does not need E911 help, and instead, help is requested of a neighbor, friend or family member that is local to the user 4 and able to assist the user 4.

Having one or more digital assistants 12 within a facility, other uses for the digital assistants 12 are anticipated such as to remind the users 4 when it is time to take medicines, to call for a ride share service, and to access a host of other resources available with each digital assistant 12 that will enhance the quality of life and safety and well-being of the users 4.

Although disclosed for use in a facility such as a home or office, it is fully anticipated that the system for requesting help be deployed in a hospital, medical complex, group home, adult living facility or nursing home. In such, the system for requesting help is capable of replacing the Panic Button (typically tethered to the bed and useless if the user 4 falls away from the bed). In such, the user 4 of such a facility is able to initiate a request for help using the preprogrammed specific utterance 5 from anywhere local to the digital assistant 12 and, after assessing the issue, the agent will call a person at the monitoring station (e.g. nurse, orderly) or a Central Monitoring station. Further, it is fully anticipated that the system for requesting help be deployed in hotels. In guest rooms equipped with the system for requesting help, in addition to summoning help should the guest have a medical emergency, sees a fire, or is being assaulted or robbed, the digital assistant 12 will control televisions, music players, wake alarms, thermostats, etc. In such, each digital assistant 12 is associated with a room number. Likewise, it is fully anticipated that the system for requesting help be deployed in commercial or business environments providing higher security and safety, distributed throughout buildings, elevators, restrooms, etc. In some embodiments, the digital assistant 12 will identify the person speaking, as well as the location of the device, using voice recognition technology. With such, a call for local, internal building security or E911 emergency help is provided by the agent as needed. It is fully anticipated that the system for requesting help be deployed in schools and universities having digital assistants 12 in classrooms and public spaces so that teachers or students are able to call for help if an active shooter is present or medical emergency occurs. In such, the digital assistant 12 is associated with the classroom number and/or location. It is also fully anticipated that the system for requesting help be deployed in vehicles of any type (e.g., cars, buses, airplanes, cruise ships) and such include GPS location capability. This provides help to a user 4 during, for example, a carjacking, medical emergency, sinking vessel, etc.

Figure 11:
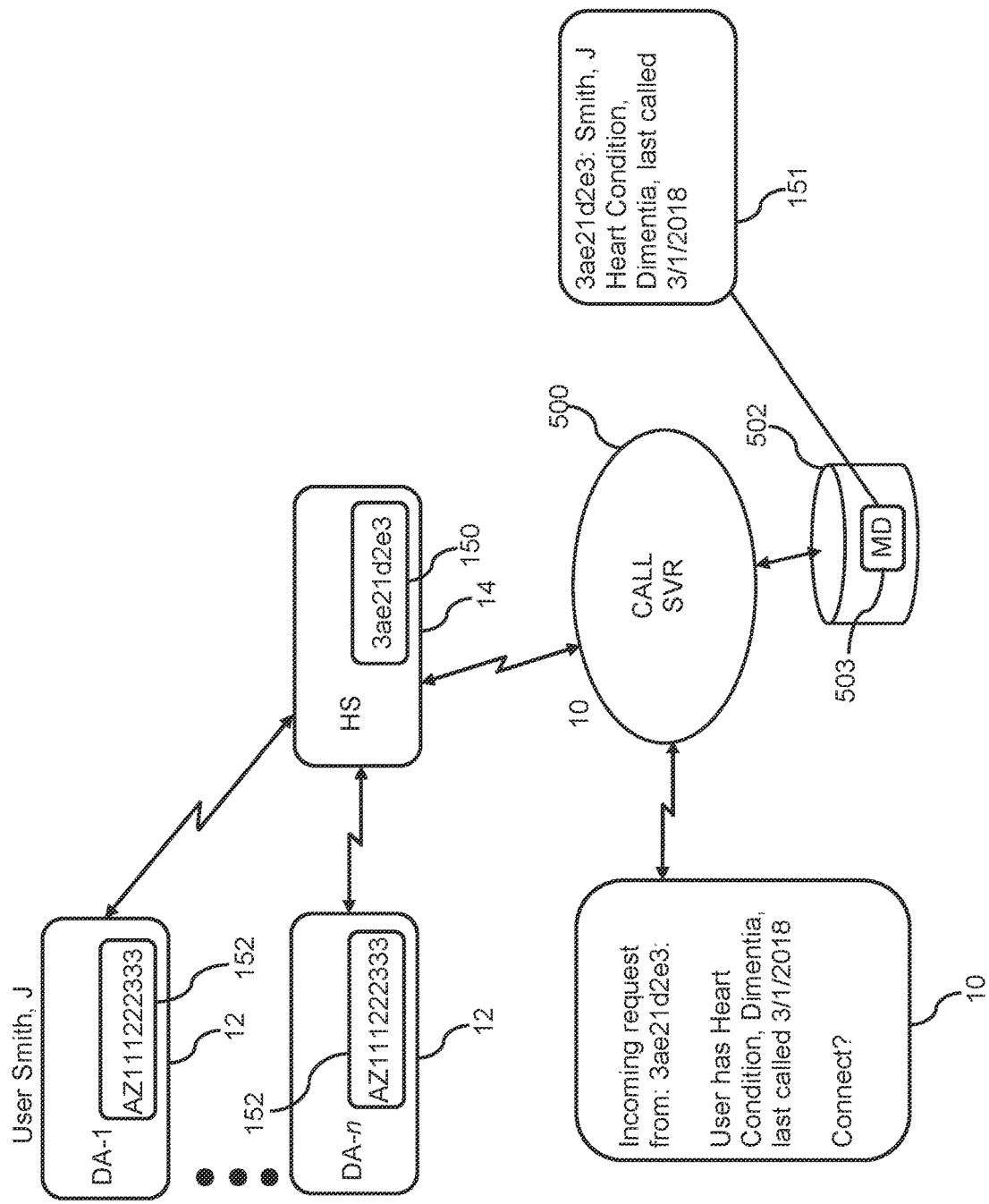
FIGS. 11 and 11A illustrate exemplary system for providing help having multiple digital assistants connected to the call server.

Referring to FIG. 11, an exemplary system for providing help having multiple digital assistants 12 connected to the call center server computer system 500 using a mobile hotspot 14 is shown. There exists a large population of potential users of the system for providing help that have limited technical abilities and, often, no Internet access or smartphone. This subset of users likely cannot setup and install the digital assistant(s) 12, even if wireless internet is available. Further, the typical setup of a digital assistant 12 often requires a smartphone, an active email address, Wi-Fi internet access, and a service account from the digital assistant provider (e.g. Amazon® or Google®). Further, a greater level of security is desired as this subset of users often is vulnerable to various intrusions. The centrally managed service described in the system and methodology provides all the required resource in pre-programmed solution which requires no installation by the user except for plugging the system into an available power outlet(s).

Digital assistant providers require a user account and an email address. To reduce the possibility of divulging private health information, an account and email address is created and both the account name and email address is randomized as part of the centrally managed system. For example, the account name is AZ111222333 and the unique user email address is AZ111222333@provider.com. In this way, there is no disclosure of a name, social security number, address, or any other identifying information to the digital assistant provider and, therefore, even if there is a security breach and information is made available to/by the digital assistant provider, it will not be associated with an identified person. For example, if a communication is intercepted and disclosed, it will be that user account AZ111222333 requested help due to chest pain, with no way for the digital assistant provider of perpetrator to know the identity of the user associated with the user account of AZ111222333.

Therefore, as shown in FIG. 11, each digital assistant 12 in the same facility (e.g. the home of J. Smith), has been pre-registered with the same digital assistant provider account 152 (e.g. AZ111222333).

In this, if the user 4 already has wireless data access (e.g. Wi-Fi), one anticipated option is to provide one or more digital assistants 12 that are preprogrammed and setup with that user's account (e.g. AZ111222333). This still requires each digital assistant 12 to recognize the user's 4 private wireless network, typically requiring a smartphone to provide a network access password to each digital assistant 12.

Figure 12:
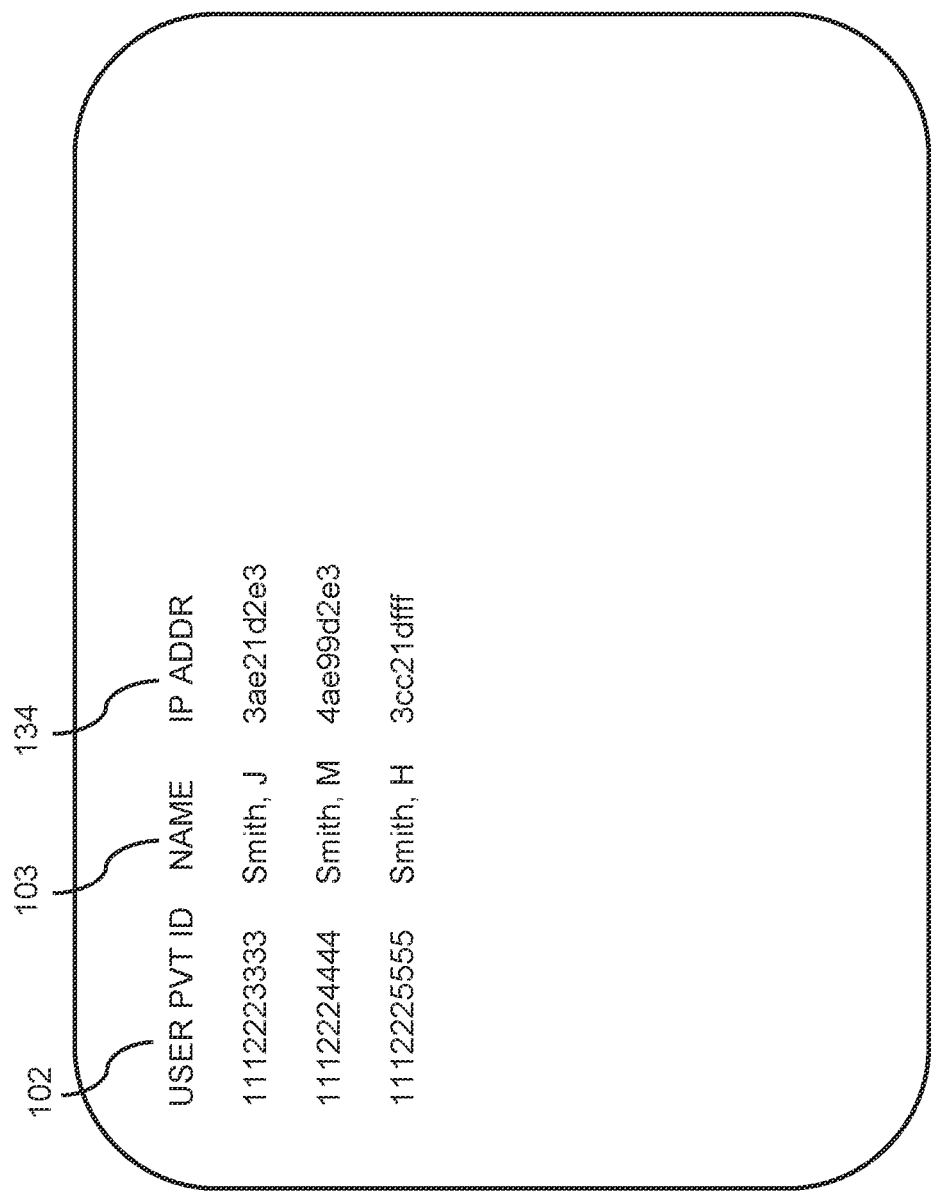
FIG. 12 illustrates an exemplary user database for translating between user accounts and unique addresses of the mobile hotspot.

To further simplify both operation and installation, an improved anticipated option is to provide a turn-key system for providing help as shown in FIG. 11, having one or more digital assistants 12 pre-configured and pre-connected to a mobile hotspot 14. In this, each digital assistant 12 is associated with a digital assistant provider account 152, each digital assistant 12 is preprogrammed with the preprogrammed specific utterance 5, and each digital assistant is pre-configured to connect to the call center server computer system 500 through the mobile hotspot 14. In addition, the mobile hotspot 14 has a unique address 150, typically known as a MAC address. When a request is received by the call center server computer system 500, the call center server computer system 500 is aware of the unique address 150 and, for example, using a translation table as shown in FIG. 12, the call center server computer system 500 is able to determine to source of the request (e.g. name 103 of requester and the account number 102 of the requester.

Further, by having the unique address 150 of each mobile hotspot 14 assigned to the user 4, additional features are enabled. One feature that is anticipated is a polling feature to make sure each mobile hotspot 14 and associated digital assistants 12 are functioning properly. For example, once per day or once per hour, the call center server computer system 500 establishes a connection to each digital assistant 12, enabled by the centrally managed system. If the connection fails, this signals a potential hardware problem and service is performed. Another feature anticipated is outward calling to each user 4. In this, the call center server computer system 500 makes an unsolicited call to the digital assistants 12 and solicits a verbal answer (e.g., "Hello J. Smith, is everything OK?"). If the appropriate verbal answer (e.g. "Yes," or "Alexa Yes") is not received within a predetermined time period, appropriate action takes place such as calling the user 4 by phone, dispatching private staff, contacting loved ones or neighbors, etc.

It is further anticipated that some portion of the user's 4 address is programmed into the user's account to enable digital assistant features that are location specific (e.g., "what is the weather?" or "what is playing at nearby movie theatres?"). It is also anticipated that if the user 4 has a smartphone, the user's smartphone be programmed with the user's account information so that the user has the ability to adjust the digital assistant, for example, by adding skills, contacts, etc.

Figure 11A:
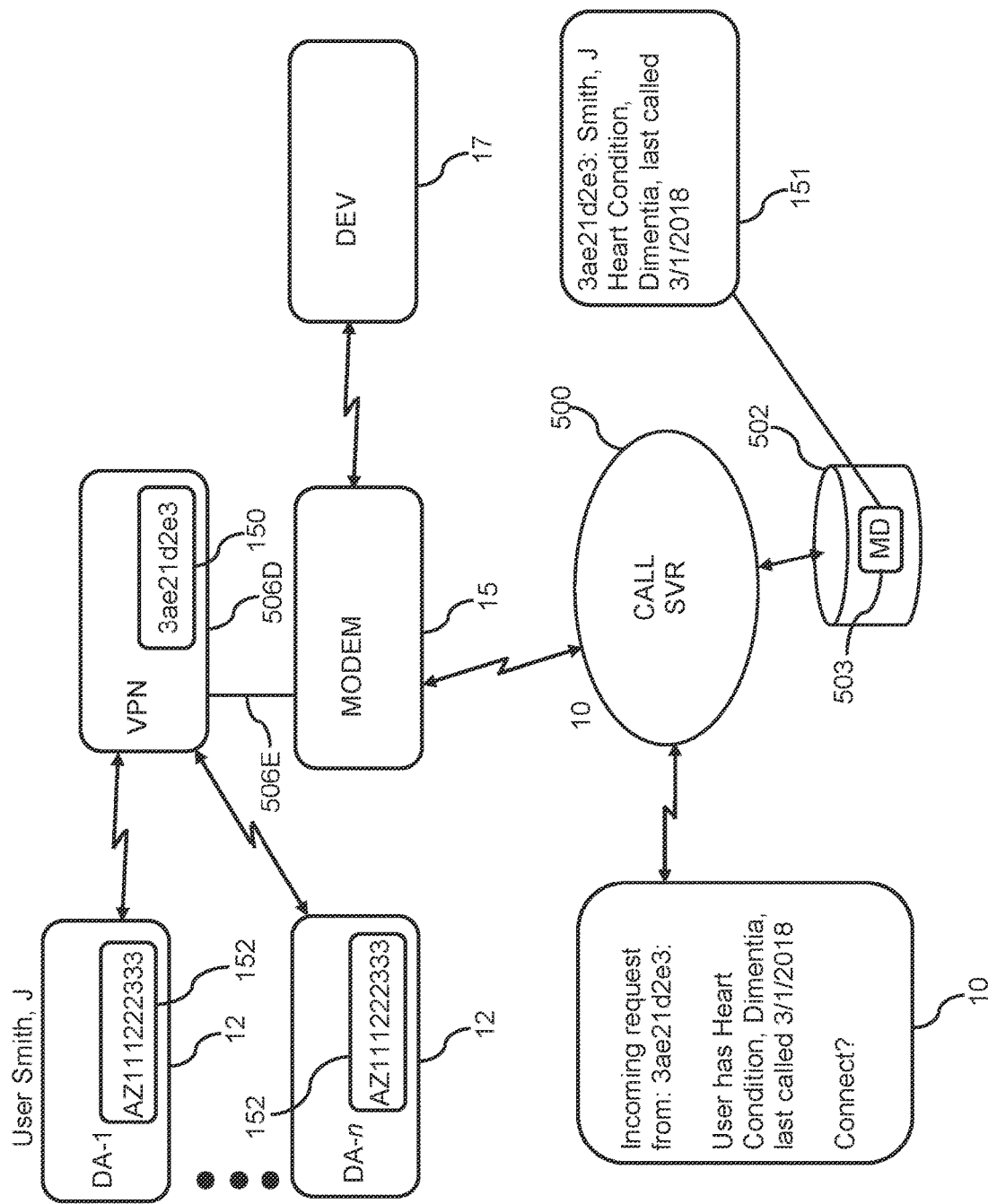

Referring to FIG. 11A, an exemplary system for providing help having multiple digital assistants 12 connected to the call center server computer system 500 using an existing modem 15 is shown. There exists a large population of potential users of the system for providing help that have limited technical abilities and, often, no Internet access or smartphone. This subset of users likely cannot setup and install the digital assistant(s) 12, even though they already have a wireless internet connected by a modem 15 (e.g. a cable modem or fiber modem). Further, the typical setup of a digital assistant 12 often requires a smartphone, an active email address, Wi-Fi internet access, and a service account from the digital assistant provider (e.g. Amazon® or Google®). Further, a greater level of security is desired as this subset of users often is vulnerable to various intrusions. The centrally managed service described in the system and methodology provides all the required resource in pre-programmed solution which requires no installation by the user except for plugging the system into an available power outlet(s).

Digital assistant providers require a user account and an email address. To reduce the possibility of divulging private health information, an account and email address is created and both the account name and email address is randomized as part of the centrally managed system. For example, the account name is AZ111222333 and the unique user email address is AZ111222333@provider.com. In this way, there is no disclosure of a name, social security number, address, or any other identifying information to the digital assistant provider and, therefore, even if there is a security breach and information is made available to/by the digital assistant provider, it will not be associated with an identified person. For example, if a communication is intercepted and disclosed, it will be that user account AZ111222333 requested help due to chest pain, with no way for the digital assistant provider of perpetrator to know the identity of the user associated with the user account of AZ111222333.

Therefore, as shown in FIG. 11A, each digital assistant 12 in the same facility (e.g. the home of J. Smith), has been pre-registered with the same digital assistant provider account 152 (e.g. AZ111222333).

In FIG. 11A, the user 4 already has wireless data access (e.g. Wi-Fi), provided by a modem 15 (e.g. cable modem or fiber modem), typically used by one or more devices 17 within the user's home. In this embodiment, one or more digital assistants 12 are provided that are preprogrammed and setup with that user's account (e.g. AZ111222333). Each digital assistant 12 is preprogrammed with credentials to connect to the virtual private network repeater 506D, providing a turn-key system for providing help as shown in FIG. 11A. In this, each digital assistant 12 is associated with a digital assistant provider account 152, each digital assistant 12 is preprogrammed with the preprogrammed specific utterance 5, and each digital assistant is pre-configured to connect to the call center server computer system 500 through the virtual private network repeater 506D and, subsequently though the user's modem 15. Note that the virtual private network repeater 506D is connected to the modem 15 by a wire 506E (e.g. an Ethernet cable), thereby not requiring any credentials (e.g. passwords) regarding the modem 15. In addition, the virtual private network repeater 506D has a unique address 150, typically known as a MAC address. When a request is received by the call center server computer system 500, the call center server computer system 500 is aware of the unique address 150 and, for example, using a translation table as shown in FIG. 12, the call center server computer system 500 is able to determine to source of the request (e.g. name 103 of requester and the account number 102 of the requester.

Further, by having the unique address 150 of each mobile virtual private network repeater 506D assigned to the user 4, additional features are enabled. One feature that is anticipated is a polling feature to make sure each virtual private network repeater 506D and associated digital assistants 12 are functioning properly. For example, once per day or once per hour, the call center server computer system 500 establishes a connection to each digital assistant 12, enabled by the centrally managed system. If the connection fails, this signals a potential hardware problem and service is performed. Another feature anticipated is outward calling to each user 4. In this, the call center server computer system 500 makes an unsolicited call to the digital assistants 12 and solicits a verbal answer (e.g., "Hello J. Smith, is everything OK?"). If the appropriate verbal answer (e.g. "Yes," or "Alexa Yes") is not received within a predetermined time period, appropriate action takes place such as calling the user 4 by phone, dispatching private staff, contacting loved ones or neighbors, etc.

It is further anticipated that some portion of the user's 4 address is programmed into the user's account to enable digital assistant features that are location specific (e.g., "what is the weather?" or "what is playing at nearby movie theatres?"). It is also anticipated that if the user 4 has a smartphone, the user's smartphone be programmed with the user's account information so that the virtual private network repeater 506D user has the ability to adjust the digital assistant, for example, by adding skills, contacts, etc.

Figure 13:
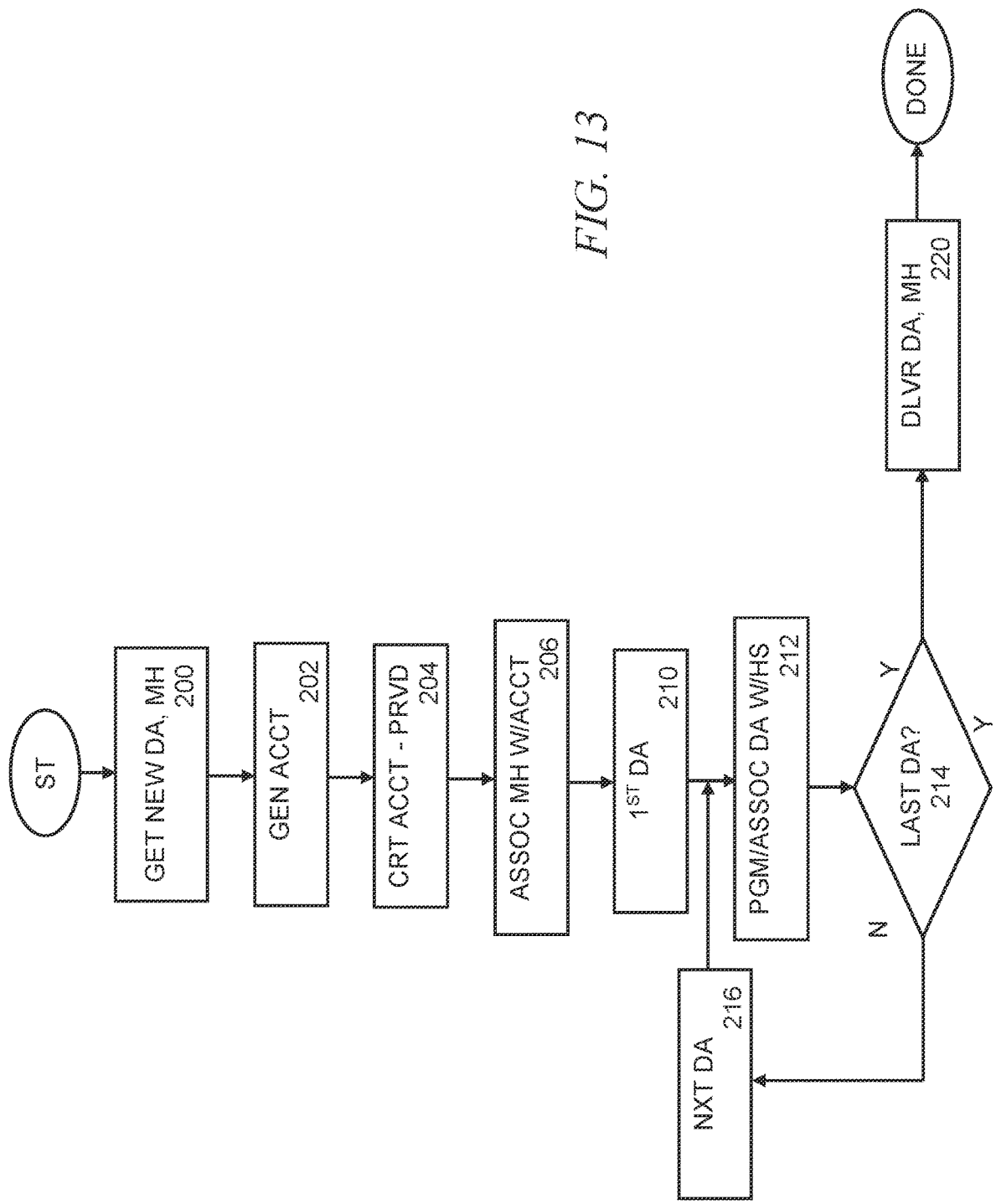
FIGS. 13 and 14 illustrate exemplary program flows of the system for requesting help.
Figure 14:
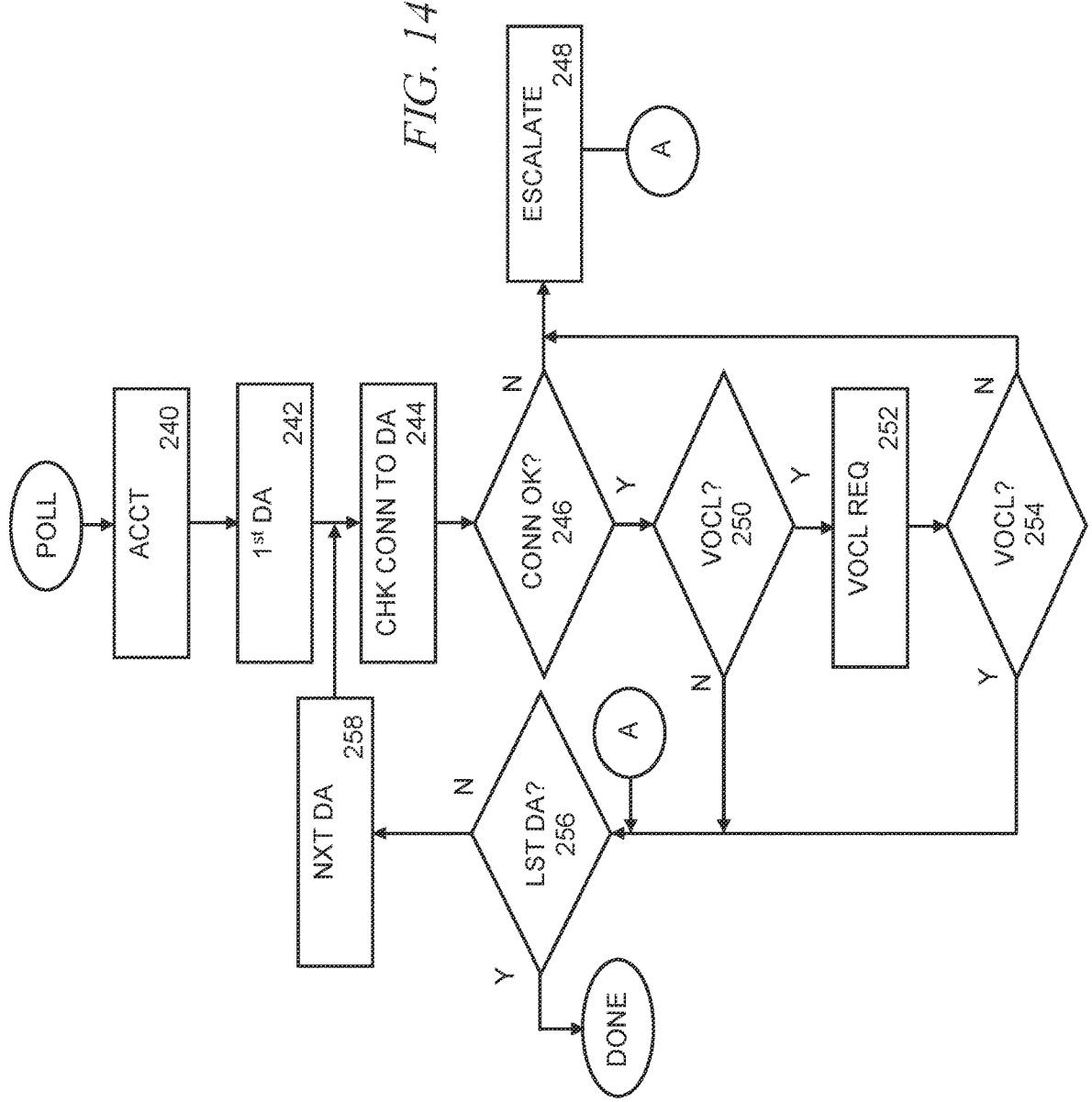

Referring to FIGS. 13 and 14, exemplary program flows of the system for requesting help are shown. In FIG. 13, a new digital assistant 12 and mobile hotspot 14 are being programmed. The first step is to get 200 a digital assistant(s) 12 and mobile hotspot 14. Now a new account is generated 202 (e.g. in the data storage 502 of the call center server computer system 500), creating the private identity 102 of the user 4 and adding user information such as the name 103 of the user 4, address 104, phone number 105, medical situations and medical information 114, and contact information 134 (e.g. local emergency contacts, neighbors, dedicated staff, private staff, etc.

Now the account is created 204 at the provider of the digital assistant 12 using private identity 102 of the user 4 and other information, for example, including minimal identifying information of the user 4 such as zip code or possibly street name, but not street number.

The mobile hotspot 14 is associated 206 with the new account, adding a unique identifier/address of the mobile hotspot 14 (e.g., MAC address and/or phone number) to the new account and, therefore, associating the mobile hotspot 14 with the new account of the user 4. Note that each mobile hotspot 14 has a unique address to the cellular network 506C, typically a phone number to which the call center server computer system 500 is able to address uniquely, for example, by sending a text message to this phone number.

Next, each digital assistant 12 is configured to communicate with the mobile hotspot 14 and to include the skills needed to provide the system for requesting help (e.g. at a minimum, the skill to recognize the preprogrammed specific utterance 5, for example, "Alexa, call for help," or "Hey XX, call for help"). As it is anticipated that a single user have one or more digital assistants 12, likely depending upon the size and layout of the facility of the user 4 (e.g. home), a loop begins with the first 210 digital assistant 12. The digital assistant 12 is programmed to be centrally managed by the provider and associated 212 with the mobile hotspot 14. The programming includes adding the skills needed to provide the system for requesting help (e.g. at a minimum, the skill to recognize the preprogrammed specific utterance 5). The association includes setting up the digital assistant 12 to properly communicate with the mobile hotspot 14. If this is the last 214 digital assistant 12 for the user 4, the digital assistant(s) 12 and mobile hotspot(s) 14 are delivered/sold 220 to the user 4 and the process is complete. If this is not the last 214 digital assistant 12, the next 216 digital assistant 12 is selected and the above steps 212/214 repeat.

In FIG. 14, a polling loop is shown, as the system for requesting help is enabled to provide monitoring of the premise equipment (e.g. digital assistant(s) 12 and mobile hotspot(s) 14). In order to provide such monitoring, the call center server computer system 500 (or other computer) needs the ability to connect to the premise equipment. In prior systems, this ability was not present, so there was no ubiquitous way to check and make sure each user's premise equipment was functioning. Now, using the mobile hotspots 14 and maintaining an address of each mobile hotspot 14, the system for requesting help is enabled to periodically reach out and make sure the premise equipment is functioning and/or make sure the user 4 is responsive.

Testing of the mobile hotspots 14 is easily performed by sending a text message to the phone number associated with each mobile hotspot 14, but this does not address each digital assistant 12.

For fully end-to-end testing, each digital assistant 12 associated with an account establishes a connection with the call center server computer system 500 (or other computer in the system) during initialization (power-up). Therefore, a user 4 that has three digital assistants 12 will have three active connections to the call center server computer system 500.

Polling of each digital assistant 12 on a list of digital assistants to poll is performed at a selected time or times of each day, for example, every day at 2:00 PM. At that time, the account on the list 240 is selected and a loop begins selecting the first 242 digital assistant 12 for the account. The account is accessed in the database to get the connection handle (e.g. connection id) and the connection is checked 244 to make sure there was no disconnect. If the digital assistant 12 is not connected 246, an escalation 248 is performed and the loop continues. The escalation 248 is, for example, an agent determines if other digital assistants 12 at the user's 4 premise are working, calls the user 4 by phone, contacts a neighbor of the user 4, contacts a provider local to the user 4, etc.

If the digital assistant 12 is connected 246, a flag is checked in the account to determine if the user 4 is configured to receive a voice prompt 250. If the user 4 is configured to receive a voice prompt 250, the voice prompt is made 252 (e.g. a verbal request such as "Good afternoon Mr. Smith. Please respond with a yes."). If the user 4 does not respond 254 with a verbal answer "yes," (perhaps within a given time allotment, the above escalation 248 is performed and the loop continues.

If the user 4 responds 254 with a verbal "yes," or "Alexa yes," the loop continues with determining if this digital assistant 12 is the last 256 digital assistant. If this digital assistant 12 is the last 256 digital assistant, the polling for this account is performed (e.g., polling for the next account is now performed, if any). If this digital assistant 12 is not the last 256 digital assistant, the next digital assistant 258 is selected and the loop continues.

Figure 15:
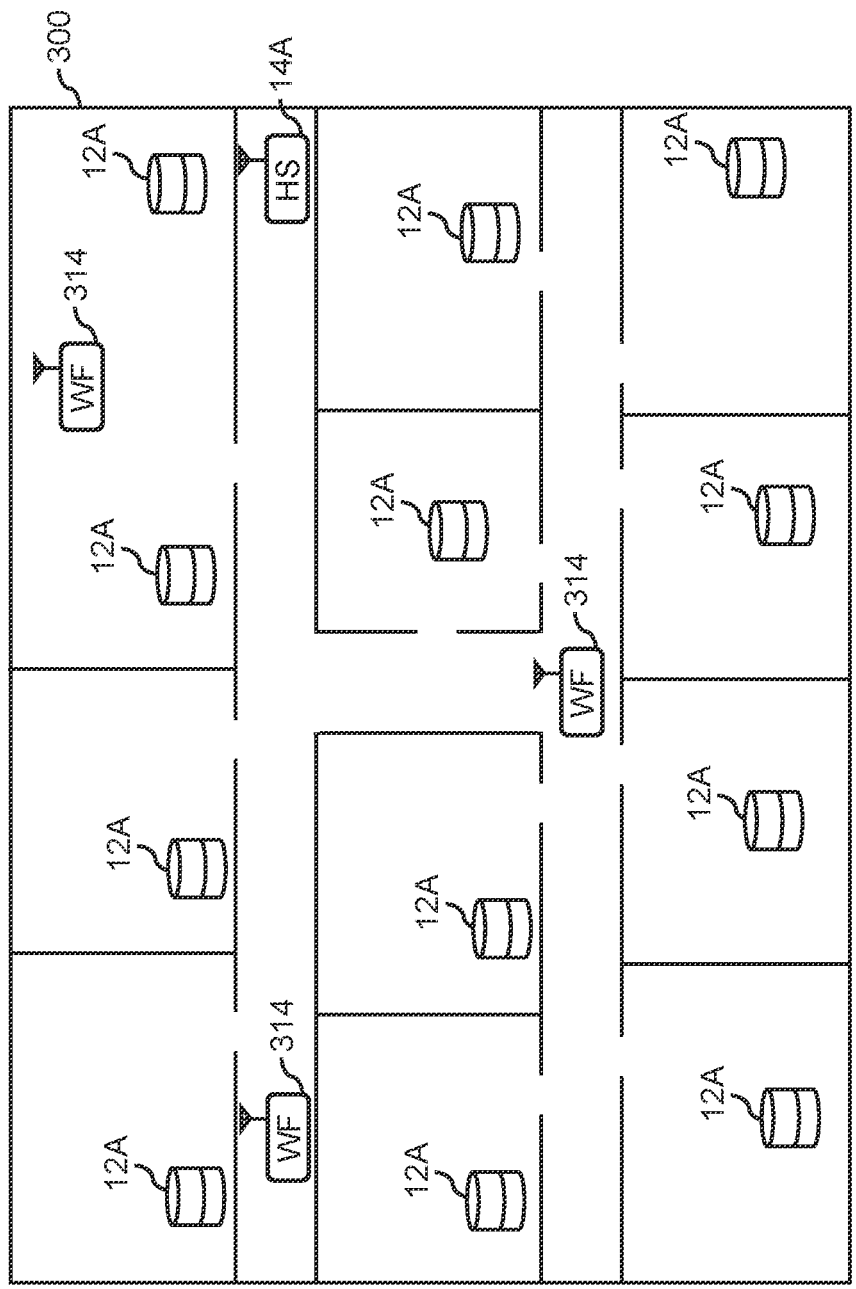
FIG. 15 illustrates an exemplary floor plan showing a facility having multiple digital assistants.

Referring to FIG. 15, an exemplary floor plan 300 within a facility (e.g. an assisted living facility) is shown having multiple battery-backed digital assistants 12A. As it is important that the battery-backed digital assistants 12A operate and communicate during power outages, each battery-backed digital assistant 12A includes a battery backup 302 (see FIG. 16) to provide operation during a power outage. Further, as a mobile hotspot 14 is not needed for each battery-backed digital assistant 12A, several battery-backed Wi-Fi transceivers/repeaters 314 are located within the facility along with at least one battery-backed hotspot 14A. Note that during a power outage, many terrestrial communications links (e.g. cable, copper, fiber) will cease communicating, but cellular systems are likely to continue working.

Therefore, even though the Wi-Fi transceivers 314 typically communicate through a terrestrial based communications link, during power outages, they will switch over to the battery-backed hotspot 14A that communicates through cellular technology.

Figure 16:
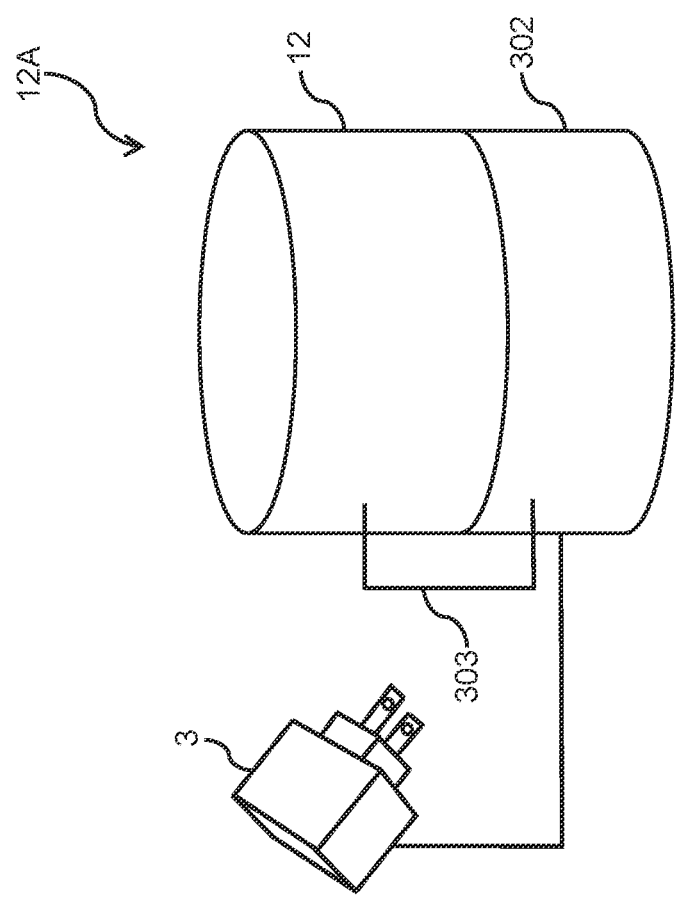
FIG. 16 illustrates a battery-backed digital assistant.

Referring to FIG. 16, a battery-backed digital assistant 12A is shown. In this, the digital assistant 12 is connected to a battery backup module 302 that, in some embodiments, is of similar shape and provides a docking-like interface on which the digital assistant 12 rests. In this example, the battery backup module 302 is powered by a wall transformer 3 and a wired connection 303 is made to the digital assistant 12.

Figure 17:
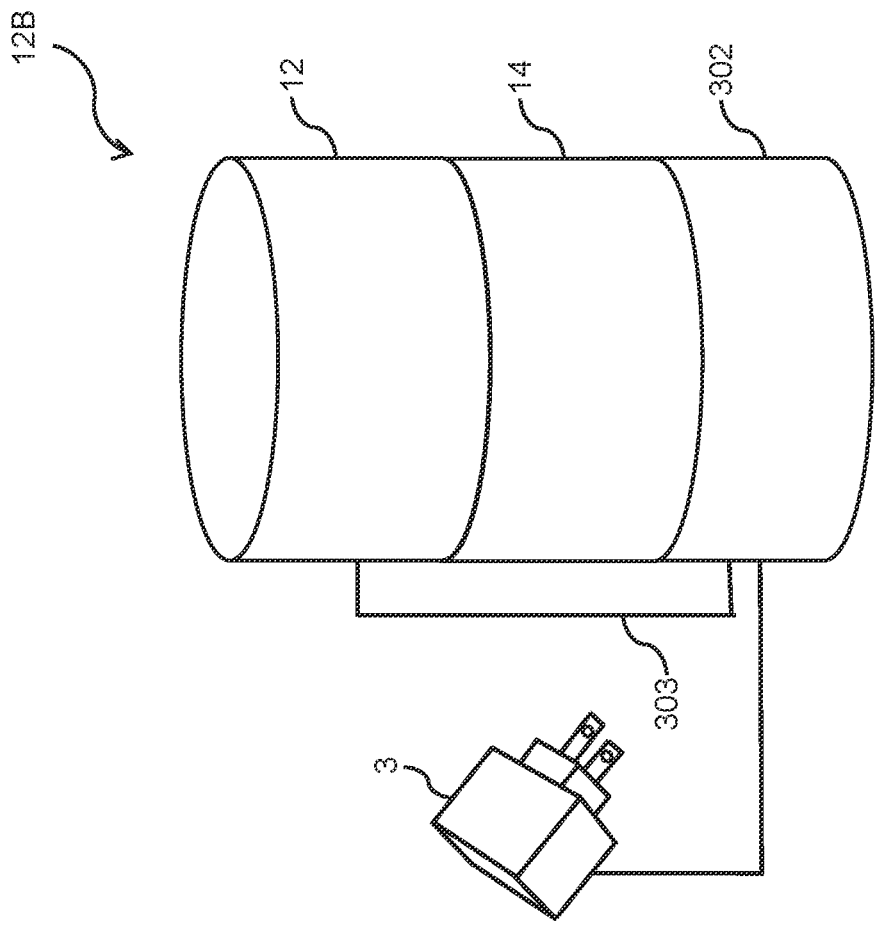
FIG. 17 illustrates a digital assistant with an integrated battery backup and hotspot.

Referring to FIG. 17, a battery-backed home digital assistant 12B is shown. In the home, it is equally important for the disclosed system to continue working even when there is a power outage. Many mobile hotspots 14 provide battery backup for short periods of time, but most digital assistants 12 do not. Therefore, in some situations, it is important to provide ample battery backup power during such power outages. The battery-backed home digital assistant 12B therefore includes a digital assistant 12, a mobile hotspot 14, and the battery backup module 302 as discussed above. In some embodiments, the mobile hotspot 14, and the battery backup module 302 are integrated into a common housing, and as above, in some such embodiments, the housing serves as a base or docking station for the digital assistant 12 which is connected to the battery backup module 302 by a wired connection 303 for power.

Figure 18:
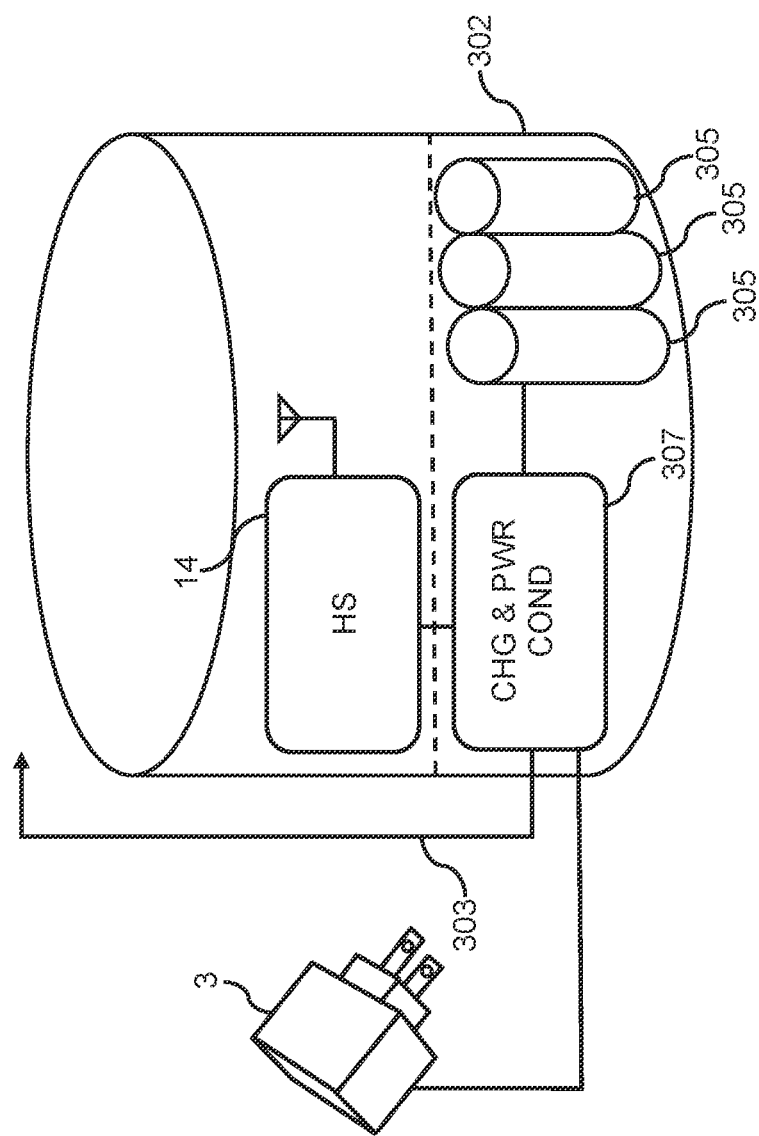
FIG. 18 illustrates a schematic view of the integrated battery backup and hotspot.

Referring to FIG. 18, a schematic of the battery-backed home digital assistant 12B is shown. The battery-backed home digital assistant 12B includes a digital assistant 12 (not shown in FIG. 18), a mobile hotspot 14, and the battery backup module 302. In some embodiments, the mobile hotspot 14, and the battery backup module 302 are integrated into a common housing, and as above, in some such embodiments, the housing serves as a base or docking station for the digital assistant 12 which is connected to the battery backup module 302 by a wired connection 303 for power.

The battery backup module includes charge control and power conditioning 307 that manages charging of the one or more internal batteries 305 and provides DC power to the digital assistant 12 through wired connection 303 as well as provides DC power to the mobile hotspot 14.

Figure 19:
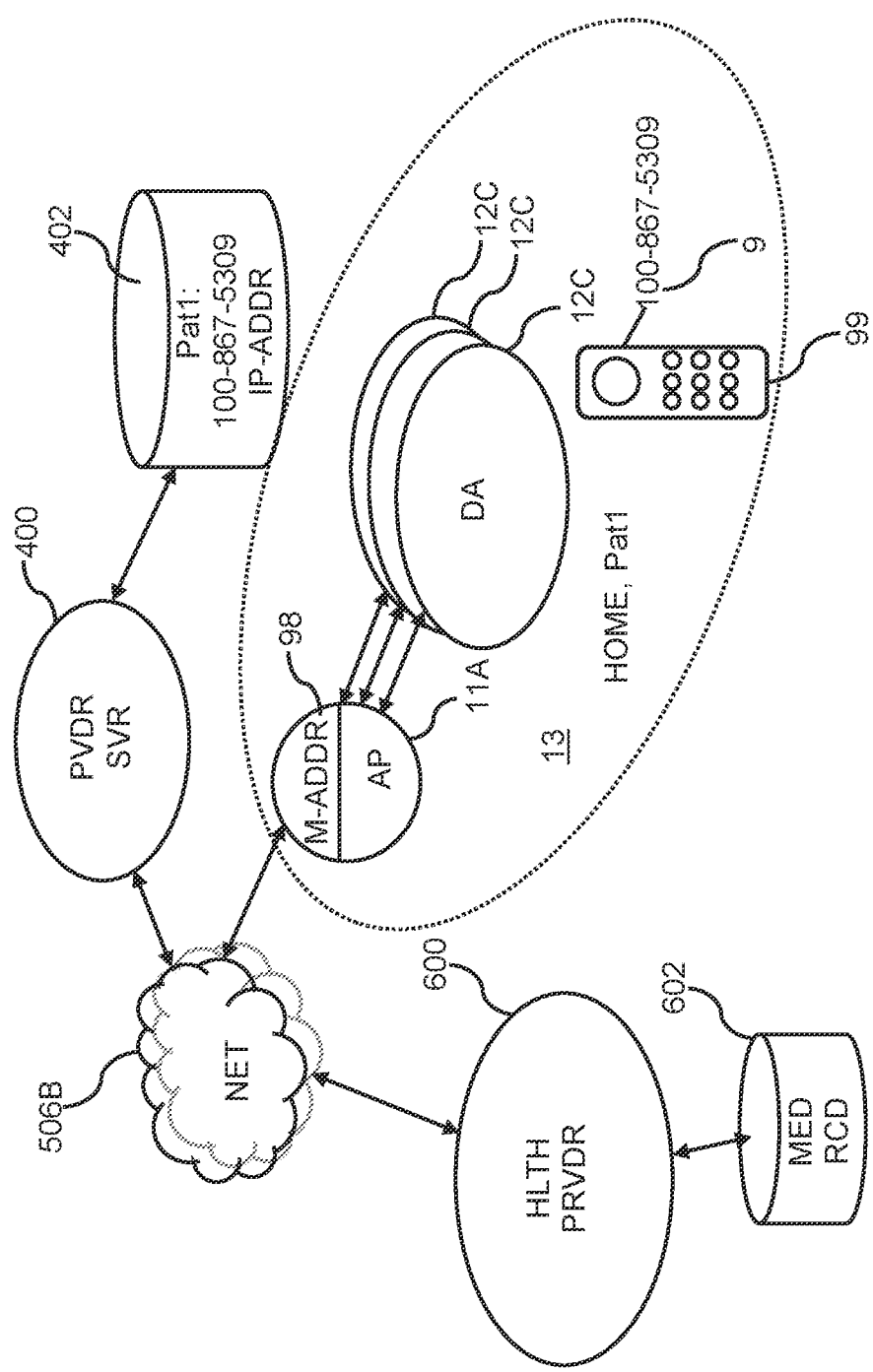
FIG. 19 illustrates a schematic view of the prior art showing an arrangement in which a digital assistant is used to call another such as health care provider.

Referring to FIG. 19, a schematic view of the prior art showing an arrangement in which a digital assistant 12C is used to place a call to another entity such as health care provider is shown. Currently, many people have one or more digital assistants 12C in their home. In such, one says the keyword (e.g. "Alexa") followed by a command (e.g. "play music by the Beatles"), and the digital assistant 12C analyzes and interprets the command and performs the requested action such as playing music, turning on/off lights, placing a voice call, etc. After purchase of the digital assistant 12C, a registration process is performed, typically at the user's home 13, to register each of the digital assistant(s) 12C with a service provider's server 400 (e.g. register an Alexa® with Amazon®) and to connect the digital assistant 12C with the user's home wireless network (note that a simplified home wireless network is shown consisting of a wireless access point 11A). During the registration process, the user typically uses an existing smartphone 99 to enter information about the user such as name, address, phone number 9 and email address. In some registration processes, the phone number 9 and email address are verified by sending a message to the smartphone by SMS, voice, or by email and requiring either an acknowledgement (response) or entering a sequence number into the registration application to confirm that the email address and phone number 9 are active and real.

The user data is stored in an account record for the user (e.g. Pat1) in a provider's database 402 associated with the service provider's server 400, including the phone number 9 and email address. During this process, the existing smartphone 99 also links the digital assistant(s) 12C to the user's wireless access point 11A.

Once the registration process is complete, the digital assistant 12C is connected to the network 506B (e.g. Internet) by way of the wireless access point 11A. Note that the wireless access point 11A has a fixed address called a MAC address 98 (M-ADDR) and an IP address. This MAC address is a unique number that is used in connecting to other devices and systems. There is a direct correlation between the MAC address and the user's wireless access point 11A, and one can likely be able to find the name of the user, and possibly the address of the user, given the MAC address 98. Also, during the registration process, the phone number 9 of the existing smartphone 99 (e.g. "100-867-5309") is captured by the service provider's server 400 and stored in the provider's database 402.

Now, when an interaction is made between the digital assistant 12C and, for example, a health care provider's system 600, the call data (e.g. voice over internet protocol data) passes through the provider's server and/or through various servers of the network 506B (e.g. Internet). In order to determine if the digital assistant 12C is authorized to perform the command (e.g. make the phone call), authorization information is exchanged between the digital assistant 12C and the service provider's server 400 to verify the digital assistant 12C. Once the call is allowed, the call to the health care provider is made (e.g. voice-over-internet protocol or VOIP or completing the call with the cellular network or land-line) and, if enabled, the health care provider receives caller identification (e.g. Caller-ID). During the call, the packetized voice passes through the network 506B and, in some situations, through the service provider's server 400. Although this data is transitory and sometimes encrypted, the encryption is weak and not very secure. Therefore, it is possible for an eavesdropper to capture the digitized and encoded voice data and decrypt the data at a later time, therefore having the ability to capture private medical information. By having the MAC address 98 (or IP address) of the user's wireless access point, the user's phone number 9, and possibly data from the user's account record in the provider's database 402, the eavesdropper is able to determine who is making the call and, therefore, knows to whom the private medical information belongs.

Figure 20:
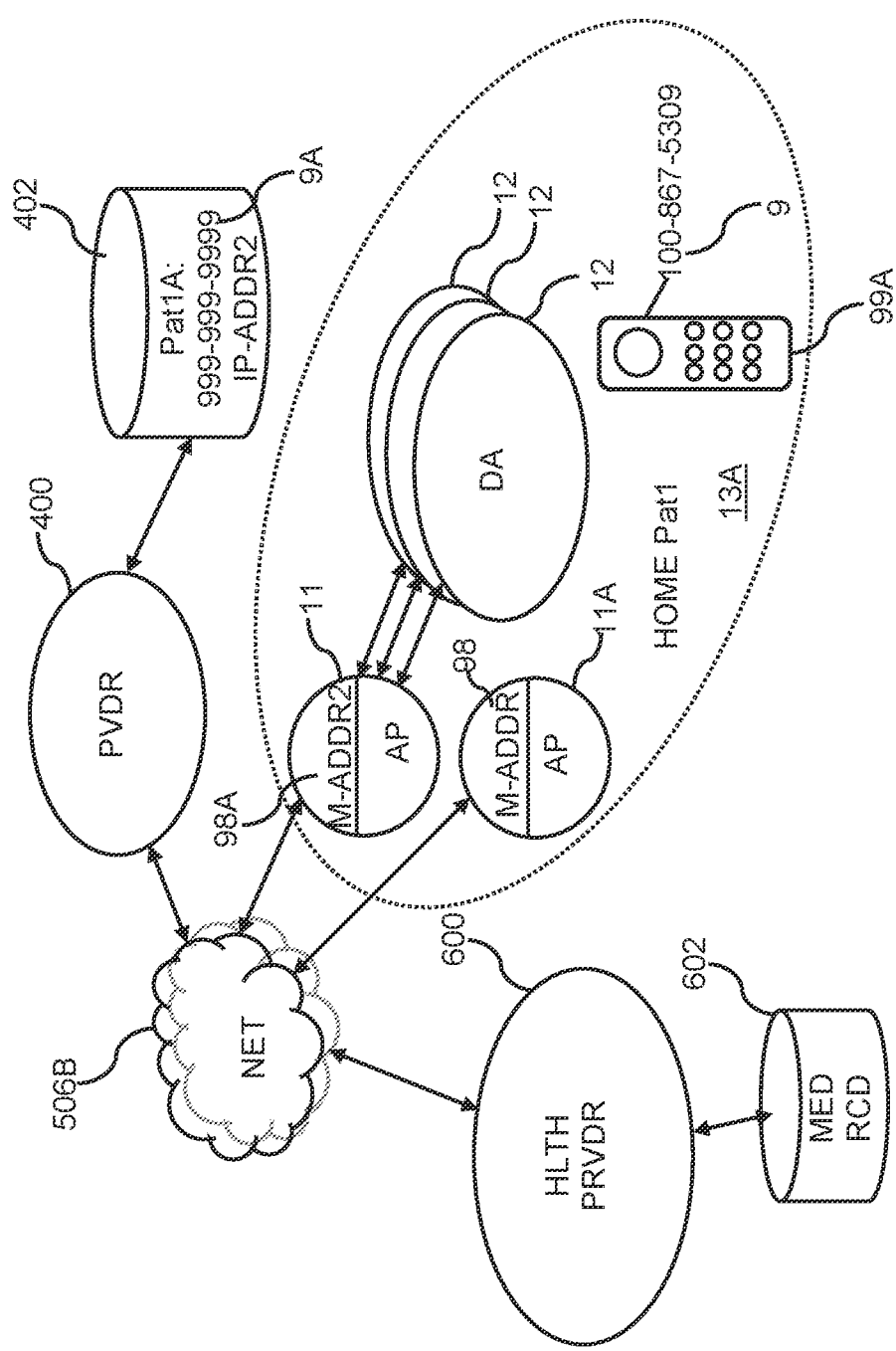
FIGS. 20 and 20A illustrate schematic views of an arrangement in which a virtualized digital assistant is used to call another such as health care provider.
Figure 20A:
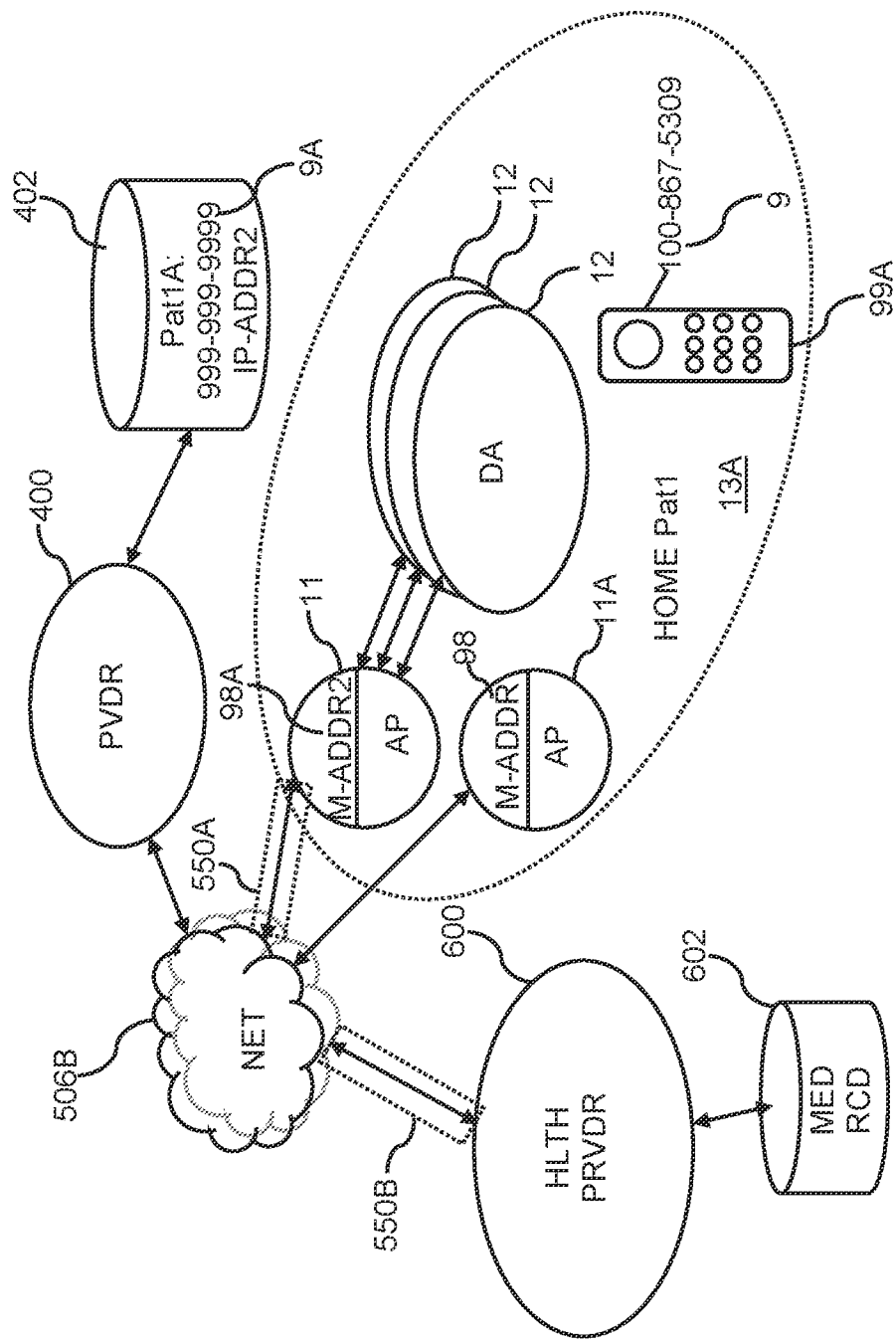

Referring to FIGS. 20 and 20A, schematic views show arrangements in which a pre-configured digital assistant 12 is virtualized and the pre-configured digital assistant 12 is used to make anonymous calls to a called party such as health care provider. As shown in FIG. 20A, in some embodiments, the connection between the dedicated access point 11 and the network 506B is made through a virtual private network 550A for added security and anonymity. Likewise, in some such embodiments, the connection between the healthcare provider's system 600 and the network 506B is also made through a virtual private network 550B for added security and anonymity.

In this example, one or more pre-configured digital assistants 12 are shown connected to a dedicated access point 11 within a home 13A (or any facility). In some such embodiments there is also another wireless access point 11A (or any network interface, all of which are optional) for general use within the home 13A or facility, for use by the user to browse the internet, read email, etc. As described previously, the pre-configured digital assistants 12 are pre-configured to operate with the dedicated access point 11 within the home and the dedicated access point 11 is pre-configured to connect to the network 506B, for example, using cellular communications provided by one or more cellular providers as, for example, a wireless access point. The dedicated access point 11 has a MAC address 98A that is not associated with the user.

When the user receives/purchases the one or more pre-configured digital assistants 12 and the dedicated access point 11, all are pre-configured to operate together. In some embodiments, the pre-configured digital assistants 12 are also programed to provide the help services described previously. In the currently described embodiment, each pre-configured digital assistant 12 is pre-programed or later programed to make calls through the network 506B, for example, to the health care provider's system 600.

This pre-configuration is performed using a dedicated phone number 9A that is not directly associated with the user. In other words, a cellular service provider provides the dedicated access point 11 having a dedicated phone number 9A that is assigned to the provider of the pre-configured digital assistants 12. The dedicated phone number 9A is different than the phone number 9 of the user's existing smartphone 99 (or phone) and has no correlation back to the user (only know to the provider of the pre-configured digital assistants 12). Therefore, any voice or data traffic between the pre-configured digital assistants 12 and, for example, the health care provider's system 600 will not include any indication of the user's phone number 9 and, therefore, cannot be correlated back to the user, thereby maintaining privacy. Likewise, during the pre-configuration process, if an email address is required, the provider of the pre-configured digital assistants 12 uses a surrogate email address that is not correlated to the user and, therefore, an eavesdropper cannot correlate any data/voice transmission back to the user by way of the email address. As the dedicated access point 11 is not actually registered to the user, any data/voice that includes the MAC address 98A or IP address (or any other addressing information) of the dedicated access point 11 cannot be correlated back to the user.

In contrast to the example of the prior art shown in FIG. 19, when one of the pre-configured digital assistants 12 is used to make a call (e.g. to the health care provider's system 600), authorization information is communicated to the service provider's server 400 to determine if a call can be made, but the authorization information does not identify the user, having a dedicated phone number 9A and an unassociated email address as were used to pre-configure the pre-configured digital assistants 12 and the dedicated access point 11. Therefore, if anyone intercepts the call and decodes the speech, they may be able to determine that some person is talking with the called party (e.g. a specific health care provider), but will not be able to identify who that person is as the phone number, email address, and MAC address of the dedicated access point 11 is that of an entity with no correlation to the user, being virtualized. For example, the dedicated phone number 9A is a virtualized phone number as it is assigned to the provider of the pre-configured digital assistants 12, not to the user.

Of course, if the user says, "hello Dr. Smith, this is Ms. Jones," the interceptor will have knowledge as to who is the initiator of the call and can correlate the medical data with the person's name. Therefore, it is preferred that the user or the called party not divulge the name of the user. To enable knowledge of who is calling, the calling phone number is the dedicated phone number 9A (e.g. 10 digits) and this number is provided to the user as a key. When the user registers with the health care provider, the user gives the health care provider this key (e.g., the dedicated phone number 9A) and the health care provider includes this key in the user's medical record 602. Later, when the user calls using the pre-configured digital assistants 12, the caller id is that of the dedicated phone number 9A and is translated by the health care provider into the user's name so the user does not need to identify themselves or minimally identity themselves (e.g. provide only first name) and the health care provider only need verify that they are talking to the anticipated user, for example, by using the user's first name. Again, any interception of voice data is useless as there is no correlation of the data to any particular user.

Figure 21:
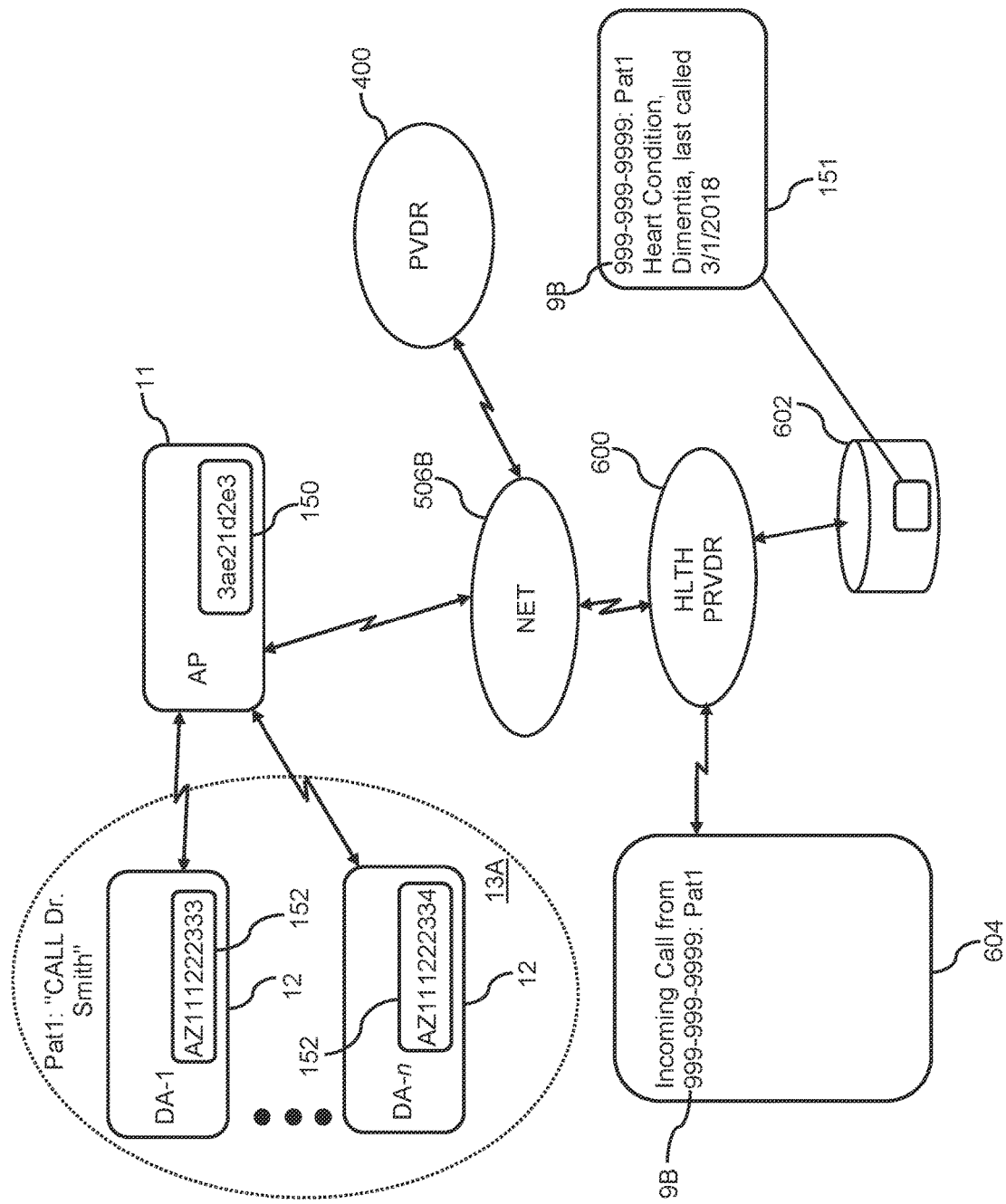
FIG. 21 illustrates a schematic view of an arrangement in which a virtualized digital assistant is used to call another such as health care provider and protected medical information is conveyed.

Referring to FIG. 21, this schematic view shows an arrangement in which a virtualized pre-configured digital assistant 12 is used to call a called party such as health care provider's system 600 and protected medical information is anonymously conveyed. In this example, the user places a voice call using one of their pre-configured digital assistants 12, for example, by saying the specific utterance 5, followed by the call command, followed by the name or number of the called party (e.g. "Alexa Call Dr. Smith"). The pre-configured digital assistant 12 communicates through the dedicated access point 11, through the network 506B, and connects with the provider's server to provide authorization for the call, to recognize the command (e.g. "call Dr. Smith") and to translate the called party (e.g. "Dr. Smith") into a called phone number. Assuming authorization passes, a phone call is made to the health care provider's system 600 (for example by Voice Over Internet Protocol-VOIP as shown, cellular or landline) and the caller-id transmitted to the called party is the dedicated phone number 9B. Once answered, the pre-configured digital assistant 12 is connected to the health care provider's system 600 (e.g. a device/server of Dr. Smith). The incoming call from the user includes a caller ID of the dedicated phone number 9B. The health care provider's system 600 utilizes user's medical record 602 to find the dedicated phone number 9B, which was provided when the user, Pat1, registered with the health care provider and is stored in a medical record 151 of the user. Note that other information is anticipated to be stored in the medical record 151 of the user such as name, date-of-birth, address, billing information, medical conditions, etc. Now, at one or more terminal devices 604 (e.g. desk phones) of the health care provider, the phone rings showing the caller-id of the dedicated phone number 9B and/or an identification of the user (e.g. "Pat1"). Now, as long as the user and whoever answers the call at the terminal device 604 does not say the full user's name, there is no way to correlate back to the user (Pat1) the data/voice exchanged between the pre-configured digital assistants 12 and the health care provider's system 600 or the health care provider's phone 99A (see FIG. 22).

Figure 22:
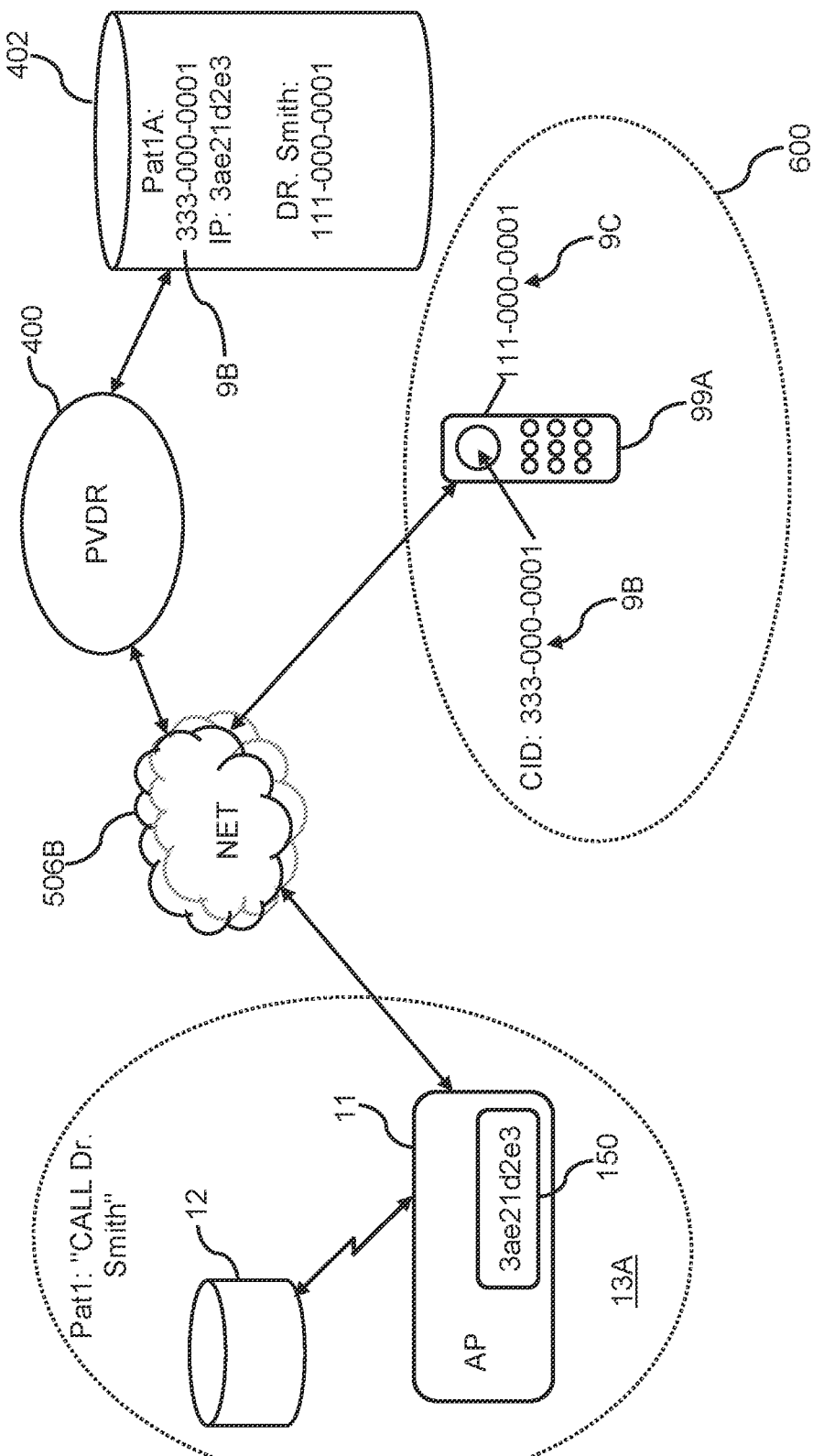
FIG. 22 illustrates a schematic view of transactions and translations made during a call protected by the virtualized digital assistant.

FIG. 22 illustrates a schematic view of transactions and translations made during an anonymous call initiated by the virtualized digital assistant. In this example, the user places a voice call their pre-configured digital assistant 12, for example, by saying the specific utterance 5, followed by the call command, followed by the name or number of the called party (e.g. "Alexa Call Dr. Smith"). The pre-configured digital assistant 12 communicates through the dedicated access point 11, through the network 506B, and connects with the service provider's server 400 to provide authorization for the call, to recognize the command (e.g. "call Dr. Smith") and to translate the called party (e.g. "Dr. Smith") into a called phone number 9C (e.g. the called number 9C of a phone 99A associated with Dr. Smith shown as 111-000-0001 as an example). Note that it is fully anticipated that the service provider's server 400 be several servers, one of which is a server operated by the manufacturer of the pre-configured digital assistants 12.

Assuming authorization passes, a phone call is made to the called phone number 9C (for example by Voice Over Internet Protocol-VOIP as shown, cellular or landline) and the caller-id transmitted in this call initiation is the dedicated phone number 9B. The called phone (e.g. a health care provider's phone 99A, a health care provider's smart speaker, or any other device capable of receiving a phone call, including devices that are also capable of sharing images and/or video) rings and shows the caller id which is the dedicated phone number 9B. Once answered, the pre-configured digital assistant 12 is connected to the called phone such as the health care provider's phone 99A of Dr. Smith. The incoming call from the user includes a caller ID of the dedicated phone number 9B and the health care provider's system 600 (including electronic and/or paper records) utilizes the dedicated phone number 9B to determine who is calling and need not require full identification of the calling party. In medical or other private communications, the dedicated phone number 9B is provided when the user, Pat1, registers, for example, with the health care provider. Now, as long as the user and whoever answers the call at the called phone (e.g. a health care provider's phone 99A) does not say the full user's name, there is no way to correlate the data/voice exchanged between the pre-configured digital assistants 12 and the called phone (e.g. a health care provider's phone 99A) back to the user (e.g., Pat1). Further, when such is a video call or a call having display sharing capabilities, the health care provider is able to show the patient imaging results, test results, etc., by way of the video or image sharing, of course redacting the patient name from the images/video shown so as to protect the identity of the patent should the images/video be intercepted.

In a similar way, the reverse scenario works equally as well. For example, when the health care provider (e.g. Dr. Smith) wants to contact the patient, Pat1, the health care provider finds the dedicated phone number 9B (for example, searching electronic and/or paper records) and dials the dedicated phone number 9B as they would have dialed the user's phone number 9 in the past. By dialing the dedicated phone number 9B, a voice connection (by any known connection means) is made between the health care provider's system 600 and/or phone 99A and the patient's virtualized pre-configured digital assistant 12. The patient is alerted of a call coming in from Dr. Smith as the caller ID of Dr. Smith is received at the patient's virtualized pre-configured digital assistant 12. After the patient answers, for example through voice command, the patient's virtualized pre-configured digital assistant 12 is in voice communications with the health care provider's system 600 and/or phone 99A without any transmission of an identity of the patient unless the patient divulges their identity.

Note that throughout this description, the patient's device is described as being a preconfigured digital assistant 12 which is defined as any device that accepts audio inputs and recognizes the specific utterance 5 and commands and operators that follow the specific utterance 5. For example, in "Alexa, call for help," the specific utterance is the name, Alexa, the command is "call" and the operator (or object of the command) is "for help." Note that many smart speakers are anticipated to provide the baseline functionality of the patient's device as well as many computers (smart phones being computers) that are enabled with the same or similar recognition technology as the preconfigured digital assistant 12. For example, several phone applications will recognize the same commands as a preconfigured digital assistant 12.

Figure 23:
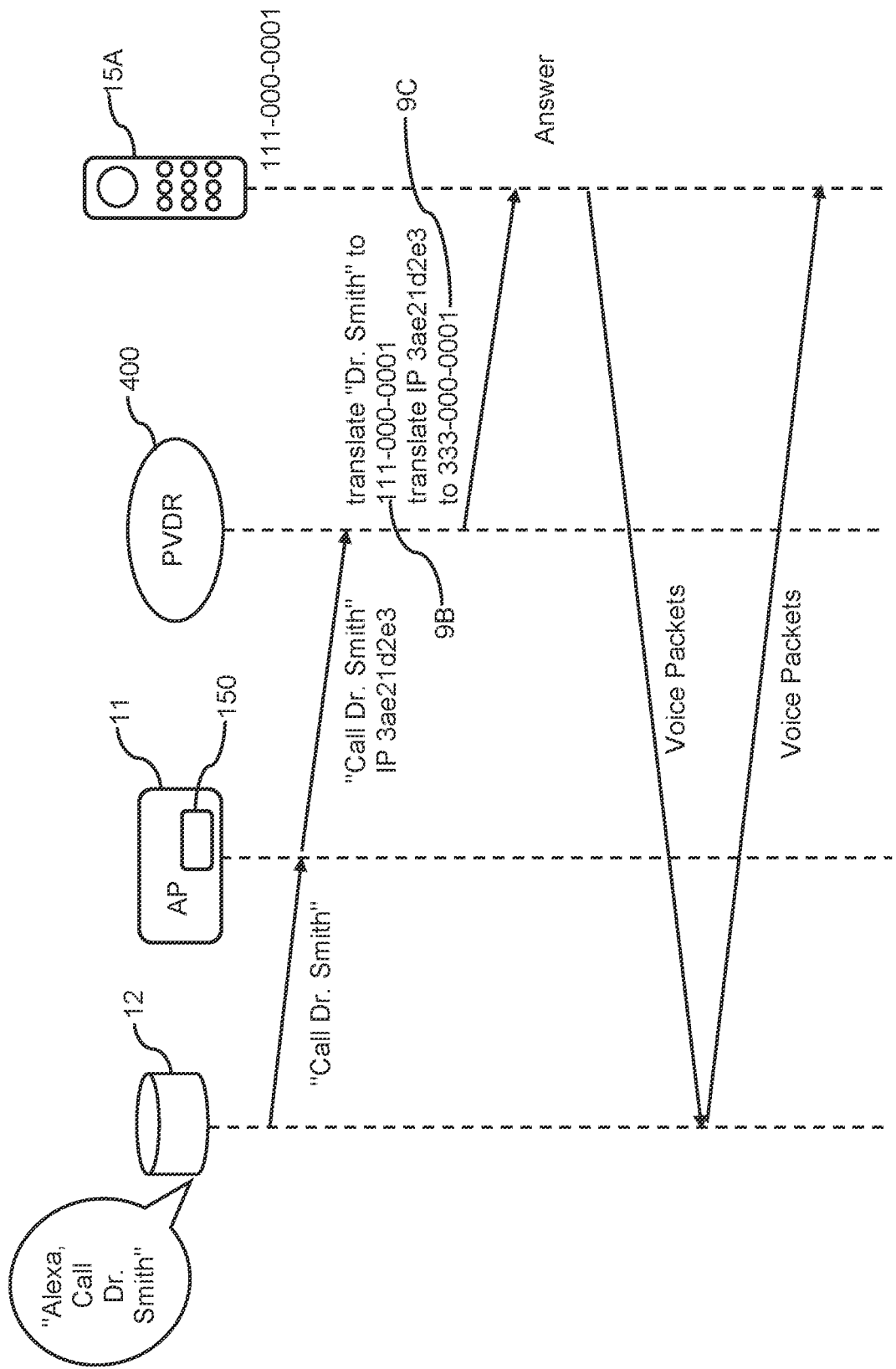
FIG. 23 illustrates transaction flow diagram, of transactions and translations made during a call protected by the virtualized digital assistant.

FIG. 23 illustrates transaction flow diagram, of transactions and translations made during a call protected by the virtualized pre-configured digital assistant 12. Microphones of the pre-configured digital assistant 12 receive audio from the user. In this case, the audio is "Alexa, Call Dr. Smith." The pre-configured digital assistant 12 recognizes the specific utterance 5, which in this example is "Alexa." The pre-configured digital assistant 12 then captures the remaining audio ("Call Dr. Smith") and either processes some or all of the audio locally or transmits the audio through the dedicated access point 11 (e.g. mobile hotspot 150) to the service provider's server 400. Note that the transaction from the dedicated access point 11 to the service provider's server 400 includes an address of the dedicated access point 11 and/or a digital assistant provider account number 152. The provider's server receives this and further recognizes the audio, breaking the command ("call") from the object of the command ("Dr. Smith") and recognizing both the command and object of the command. The provider's server then translates the object of the command (e.g. "Dr. Smith") into a phone number of such, the called phone number 9B. The service provider's server 400 then translates the identifying information of the dedicated access point 11 and/or the pre-configured digital assistant 12 into the dedicated phone number 9C. The service provider's server 400 then initiates a phone call to the called phone number 9B through any phone network of combination thereof, including Voice over Internet Protocol, Cellular, and land lines. The caller-id information provided in this phone call is the dedicated phone number 9C. Therefore, the caller id information displayed at the called phone 15A is "333-000-0001", which is the dedicated phone number 9C which is not directly associated with the user who is placing the call. The called party is able to determine who is calling if they were previously provided the dedicated phone number 9C and created a local data record that translates the dedicated phone number 9C into information about the user. In some examples of even higher security, the called party only knows the dedicated phone number 9C and is able to access medical records of the user, but for added security, the called party is not privy to the name or other demographic information about the user and, therefore, can discuss the medical information without knowing with whom they are discussing the information. As everything is virtualized except for the dedicated phone number 9C, it is as if the user called the health care provider from a pay phone and didn't identify themselves except for telling the called party the dedicated phone number 9C. Therefore, any eavesdropper would only hear (or intercept data packets) between an unknown person and the called party, not being able to determine with whom the called party (e.g. health care provider) is speaking.

As an example, if a movie star calls a cosmetic surgery office using the disclosed system and the cosmetic surgery office does not include the movie star's name or other demographic information in generally accessible data queries, the nurse or assistant receiving this call will only know the medical information that is presented such as procedure being performed, date and time of the procedure, billing records, etc. In this way, even the nurse or assistant will only know that they are talking to someone who is having a facelift on Friday, August 13th . . . In this way, it is even more difficult for others (e.g. the press) to find out what famous movie stars are having cosmetic surgery and when, etc.

In some usage scenarios, configuration and ownership of the pre-configured digital assistants 12 and the dedicated access point 11 with which the pre-configured digital assistants 12 are pre-configured to operate are leased to health care providers. In such, the company providing the pre-configured system to the health care provider manages the security, in that, the virtualization of each pre-configured digital assistant 12, phone numbers, dedicated access points 11 (including mobile hotspots 14) is performed by the company that maintains ownership (the provider) and the health care provider then distributes each pre-configured digital assistant 12 and dedicated access points 11 (including mobile hotspots 14) to patients, retaining knowledge of the phone number at the health care provider so that employees of the company that maintains ownership (employees of the provider) have no way of knowing the identity of the patient who is assigned the pre-configured digital assistant 12 and dedicated access points 11 (including mobile hotspots 14). Therefore, only the health care provider has knowledge of the identity of the patient at the pre-configured digital assistant 12 and any interception of voice or data between the health care provider and the patient cannot be associated with any particular person or patient.

Equivalent elements can be substituted for the ones set forth above such that they perform in substantially the same manner in substantially the same way for achieving substantially the same result.

It is believed that the system and method as described and many of its attendant advantages will be understood by the foregoing description. It is also believed that it will be apparent that various changes may be made in the form, construction and arrangement of the components thereof without departing from the scope and spirit of the invention or without sacrificing all of its material advantages. The form herein before described being merely exemplary and explanatory embodiment thereof. It is the intention of the following claims to encompass and include such changes.

What is claimed is:

1. A system for anonymous communications from a user to a called party, the system comprising:
    a digital assistant, the digital assistant is preprogrammed with account information and a skill for recognizing a preprogrammed specific utterance, the digital assistant configured with a dedicated phone number that is not assigned to the user;
    a wireless access point, the digital assistant configured to wirelessly communicate with the wireless access point, the wireless access point connected to the Internet such that, the digital assistant is enabled to communicate with the Internet through the wireless access point;
    whereas when the digital assistant recognizing the specific utterance followed by an indication of the called party, the digital assistant initiates a voice connection to the called party through the Internet, wherein the voice connection is initiated using the dedicated phone number which is not associated with an identity of the user;
    whereas when the called party receives caller-id data regarding the voice connection, the caller-id data comprises the dedicated phone number; and
    whereas after accepting the voice connection, the user is in audio communication with the called party.

2. The system of claim 1, whereas, the dedicated phone number is provided to the called party during a registration process of the called party.

3. The system of claim 2, whereas, knowing the dedicated phone number, the called party is enabled to correlate the dedicated phone number to a data record of the user, thereby the called party knows an identity of the user.

4. The system of claim 2, wherein the called party is a health care provider.

5. A method for providing anonymous communications from a user to a called party, the method comprising:
    obtaining a dedicated phone number;
    creating a user account for the user and assigning the dedicated phone number to the user account;
    creating a provider account for a digital assistant using the dedicated phone number;
    preprogrammed the digital assistant with the user account;
    preprogramming the digital assistant with a skill for recognizing a specific utterance;
    providing a connectivity between the digital assistant and an Internet;
    the digital assistant listening for the specific utterance and, upon recognizing the specific utterance, followed by an identification of the called party, the digital assistant initiating a voice call through the Internet to the called party, wherein the initiating of the voice call uses the dedicated phone number which is not associated with an identity of the user.

6. The method of claim 5, wherein the step of providing the connectivity comprises providing a mobile hotspot that is assigned the dedicated phone number.

7. The method of claim 5, wherein the dedicated phone number is not assigned to the user.

8. The method of claim 5, wherein during initiating the voice call through the Internet to the called party, caller-id information is provided to the called party and the caller-id information comprises the dedicated phone number.

9. The method of claim 8, further comprising before the step of initiating the voice call through the Internet, the steps of:
    providing the dedicated phone number to the called party; and
    the called party storing the dedicated phone number in a data record associated with the user.

10. The method of claim 9, further comprising after the step of initiating the voice call through the Internet, the steps of:
    the called party receiving the caller-id; and
    the called party finding the data record associated with the caller-id, thereby identifying the user.

11. The method of claim 10, wherein the called party is a health care provider and the data record comprises a medical record of the user.

12. The method of claim 5, further comprising creating a dedicated email address for use during the step of preprogrammed the digital assistant with the user account, the email address unassociated with the user.

13. A system for providing anonymous communications from a user to a called party, the system comprising:
    a dedicated phone number is obtained for the user and the dedicated phone number is not directly associated to an identity of the user to protect privacy of the user;
    a provider account created using the dedicated phone number to protect the privacy of the user;
    an account for the user created in the system for providing help, the account having information regarding the user and the account having the dedicated phone number;
    a digital assistant preprogrammed with a skill recognizing a specific utterance and the digital assistant is preconfigured to connect to an Internet;
    whereas after the specific utterance followed by an identification of the called party is detected by the digital assistant, the digital assistant initiates a voice call through the Internet to the called party, wherein the voice connection is initiated using the dedicated phone number which is not associated with an identity of the user.

14. The system of claim 13, further comprising a mobile hotspot, the mobile hotspot assigned the dedicated phone number and the mobile hotspot providing connectivity between the digital assistant and the Internet.

15. The system of claim 13, wherein when voice data transmitted over the voice call is intercepted by the eavesdropper, the eavesdropper is precluded from identifying the user by way of the dedicated phone number that is not assigned to the user.

16. The system of claim 13, whereas, the dedicated phone number is provided to the called party during a registration process of the called party.

17. The system of claim 16, whereas, knowing the dedicated phone number, the called party is enabled to correlate the dedicated phone number to a data record of the user, thereby the called party knows an identity of the user.

18. The system of claim 16, wherein the called party is a health care provider.

19. The system of claim 16, wherein the called party is enabled to call the user using the dedicated phone number.

\* \* \* \* \*